(12) United States Patent
Biedermann et al.

(10) Patent No.: US 11,278,278 B2
(45) Date of Patent: Mar. 22, 2022

(54) SURGICAL STAPLE AND INSTRUMENT FOR HOLDING AND IMPLANTING THE SURGICAL STAPLE

(71) Applicant: Biedermann Technologies GmbH & Co. KG, Donaueschingen (DE)

(72) Inventors: Lutz Biedermann, VS Villingen (DE); Timo Biedermann, Trossingen (DE); Achim Zipse, Baden-Baden (DE); Gael Dreher, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 68 days.

(21) Appl. No.: 16/944,821

(22) Filed: Jul. 31, 2020

(65) Prior Publication Data

US 2020/0352564 A1 Nov. 12, 2020

Related U.S. Application Data

(63) Continuation of application No. 16/134,111, filed on Sep. 18, 2018, now Pat. No. 10,874,389, which is a
(Continued)

(30) Foreign Application Priority Data

May 20, 2015 (EP) .................................... 15168542

(51) Int. Cl.
*A61B 17/064* (2006.01)
*A61B 17/08* (2006.01)
(Continued)

(52) U.S. Cl.
CPC ........ *A61B 17/0642* (2013.01); *A61B 17/064* (2013.01); *A61B 17/0682* (2013.01);
(Continued)

(58) Field of Classification Search
CPC .............. A61B 17/064; A61B 17/0642; A61B 17/0645; A61B 17/0682; A61B 17/083; A61B 17/809
See application file for complete search history.

(56) References Cited

U.S. PATENT DOCUMENTS 3,095,393 A 6/1963 Matt
4,263,903 A 4/1981 Griggs
(Continued)

FOREIGN PATENT DOCUMENTS

DE 4110123 A1 10/1992
DE 19821680 C1 8/1999
(Continued)

OTHER PUBLICATIONS

European Search Report and Search Opinion for EP 15168542.7 mailed by the EPO dated Nov. 9, 2015 (11 pages).
(Continued)

*Primary Examiner* — Larry E Waggle, Jr.
(74) *Attorney, Agent, or Firm* — Gordon & Jacobson, P.C.

(57) ABSTRACT

A surgical staple insertion system for compressing bone fragments includes a staple and an insertion tool. The staple has first and second legs and an elastically deformable bridge monolithically formed with the first and second legs. In a relaxed configuration, the free ends of the first and second legs are positioned closer to one another than are portions of the first and second legs connected to the bridge. The insertion tool retains the bridge in an elastically deformed configuration with the legs positioned relatively farther apart from one another during at least portion of the step of implantation of the staple. Then, the insertion tool is released from the staple so that the bone fragments between the legs are subject to compression.

27 Claims, 29 Drawing Sheets

Related U.S. Application Data continuation of application No. 15/161,124, filed on May 20, 2016, now Pat. No. 10,105,134.

(60) Provisional application No. 62/164,402, filed on May 20, 2015.

(51) Int. Cl.
*A61B 17/80* (2006.01)
*A61B 17/068* (2006.01)
*A61B 17/00* (2006.01)

(52) U.S. Cl.
CPC .......... *A61B 17/083* (2013.01); *A61B 17/809* (2013.01); *A61B 2017/0053* (2013.01); *A61B 2017/00858* (2013.01); *A61B 2017/00867* (2013.01); *A61B 2017/0645* (2013.01)

(56) References Cited

U.S. PATENT DOCUMENTS

| | | | |
|---|---|---|---|
| 4,438,769 | A | 3/1984 | Pratt et al. |
| 4,570,623 | A | 2/1986 | Ellison et al. |
| 5,454,814 | A | 10/1995 | Comte |
| 5,634,926 | A | 6/1997 | Jobe |
| 5,785,713 | A | 7/1998 | Jobe |
| 6,325,805 | B1 | 12/2001 | Ogilvie et al. |
| 6,908,467 | B2 | 6/2005 | Ip et al. |
| 7,618,441 | B2 | 11/2009 | Groiso |
| D676,962 | S | 2/2013 | Cheney et al. |
| 8,596,514 | B2 | 12/2013 | Miller |
| 9,675,344 | B2 | 6/2017 | Combrowski et al. |
| 2002/0111641 | A1 | 8/2002 | Peterson et al. |
| 2012/0024937 | A1 | 2/2012 | Allen |
| 2012/0228355 | A1 | 9/2012 | Combrowski et al. |
| 2013/0026206 | A1 | 1/2013 | Fox |
| 2013/0231667 | A1 | 9/2013 | Taylor et al. |
| 2014/0097228 | A1 | 4/2014 | Taylor et al. |
| 2014/0277516 | A1 | 9/2014 | Miller et al. |
| 2014/0358187 | A1 | 12/2014 | Taber et al. |
| 2016/0199060 | A1 | 7/2016 | Morgan et al. |
| 2016/0338697 | A1 | 11/2016 | Biedermann et al. |
| 2017/0000482 | A1 | 1/2017 | Averous et al. |
| 2019/0069892 | A1 | 3/2019 | Biedermann et al. |

FOREIGN PATENT DOCUMENTS

| | | |
|---|---|---|
| EP | 0503271 A2 | 9/1992 |
| EP | 3095393 A1 | 11/2016 |
| FR | 2725126 A1 | 4/1996 |
| FR | 2926453 A1 | 7/2009 |
| FR | 2999069 A1 | 6/2014 |
| GB | 2471648 B | 1/2011 |
| WO | WO92/17122 A2 | 10/1992 |
| WO | WO 2010/004602 A1 | 1/2010 |
| WO | WO 2016007624 A1 | 1/2016 |
| WO | WO 2016154417 A1 | 9/2016 |

OTHER PUBLICATIONS

Extended European Search Report of Application No. 18179393.6 dated Nov. 29, 2018.
U.S. Pat. No. 503,271; Aug. 15, 1893; Ortloff.

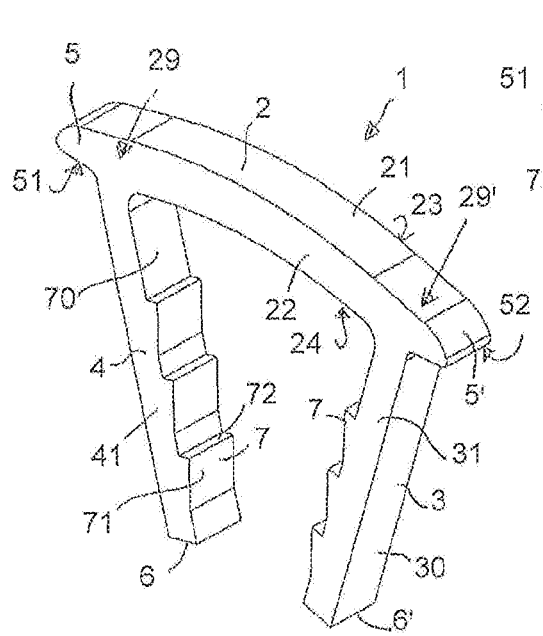
Fig. 1a
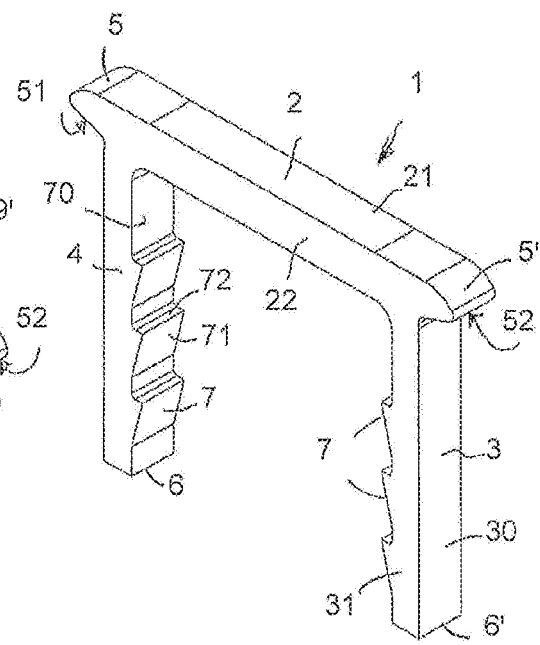
Fig. 1b
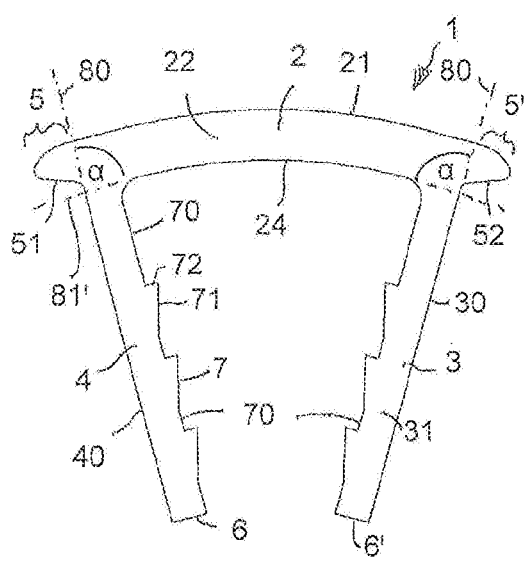
Fig. 1c
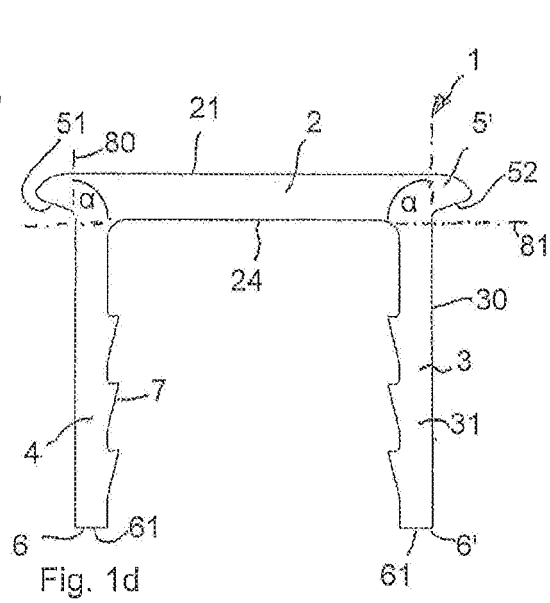
Fig. 1d
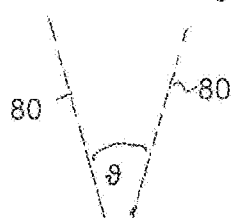

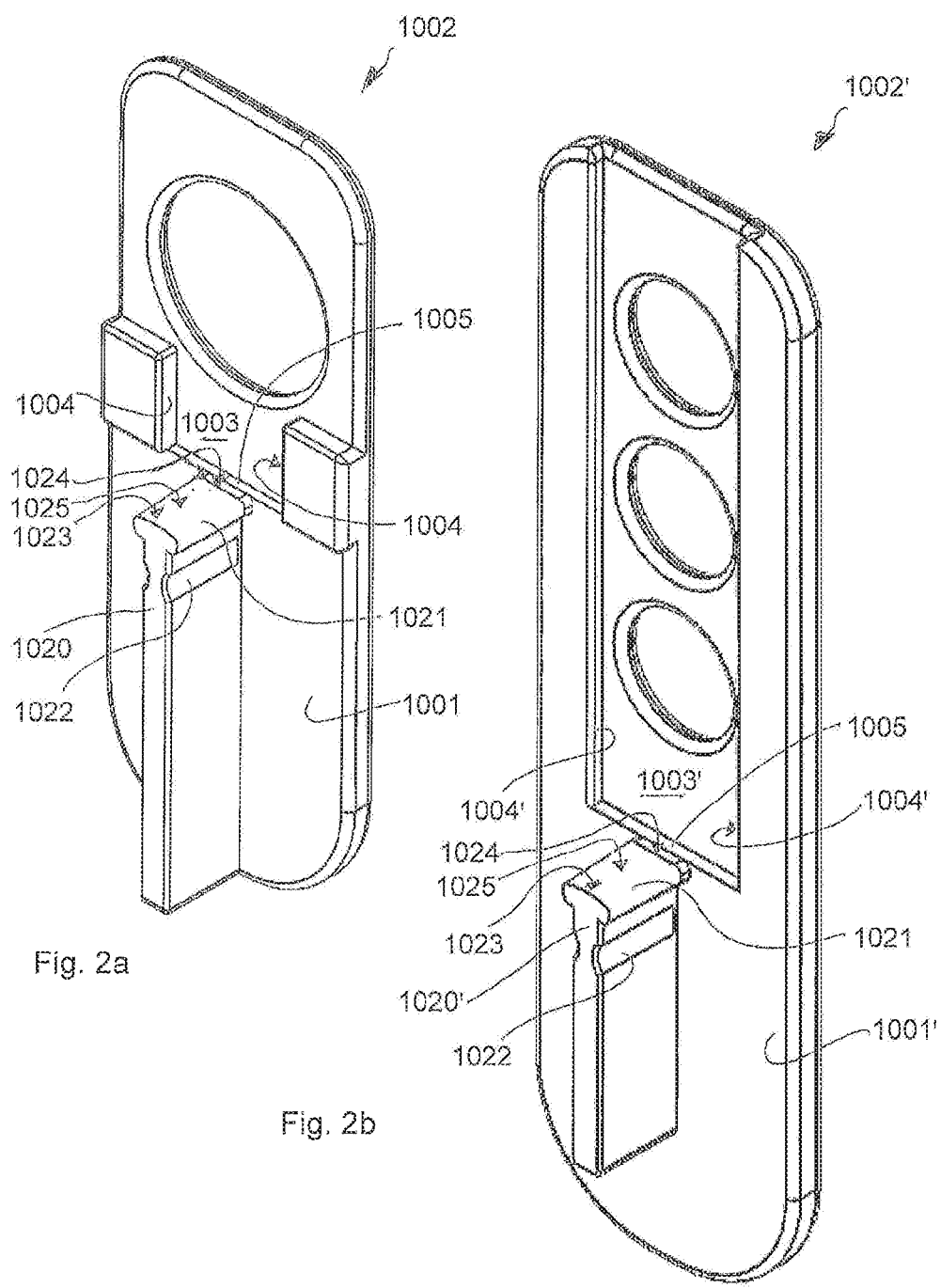

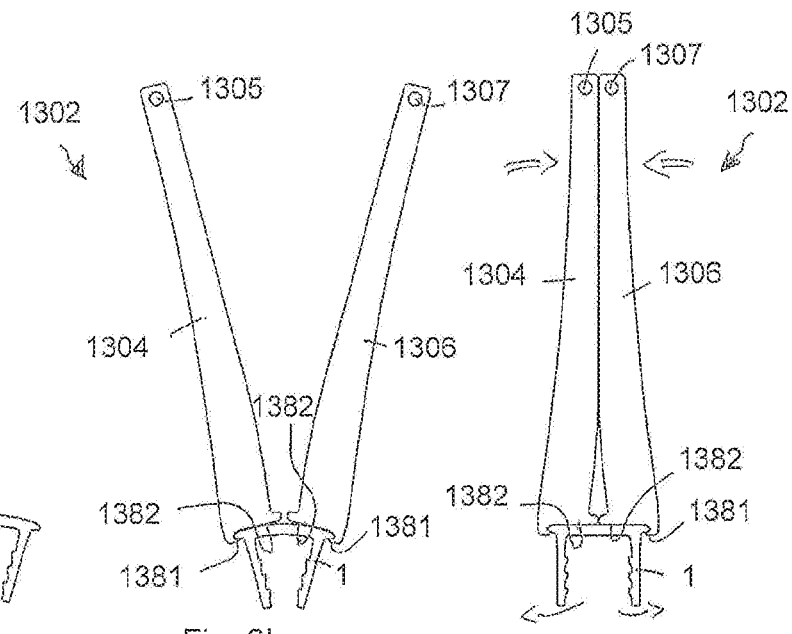
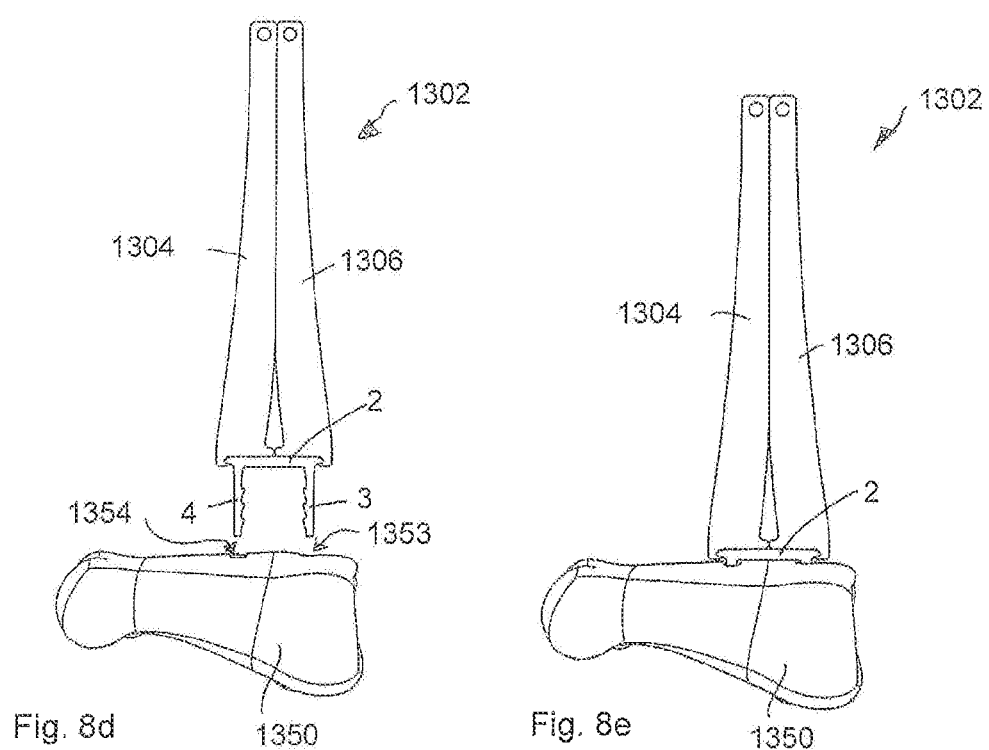

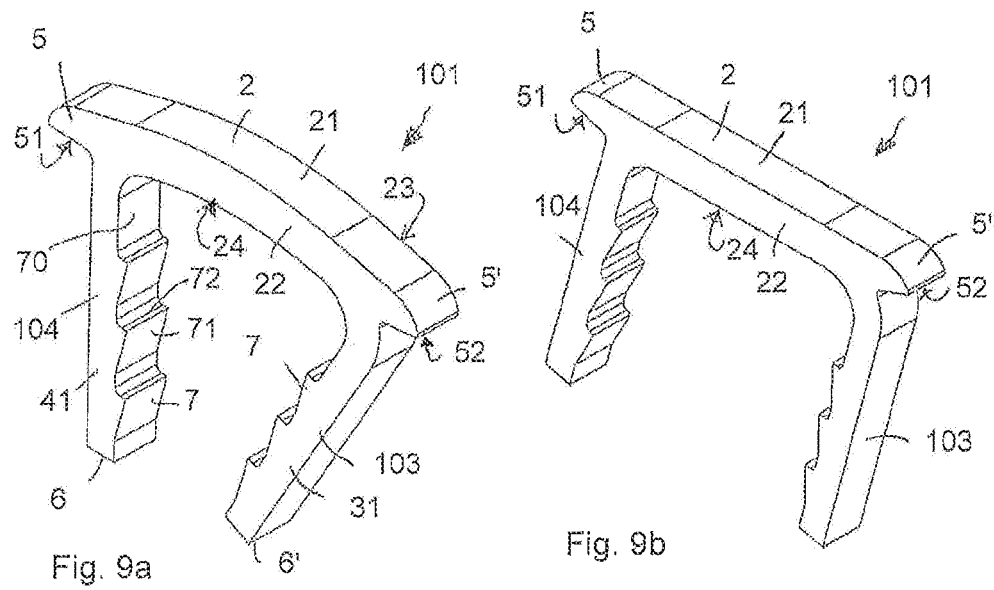
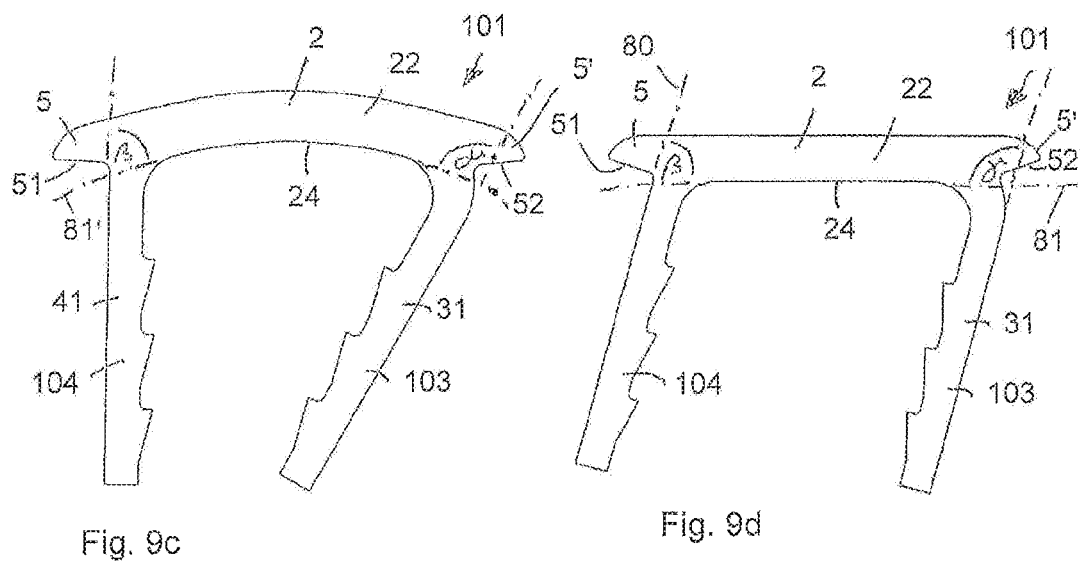

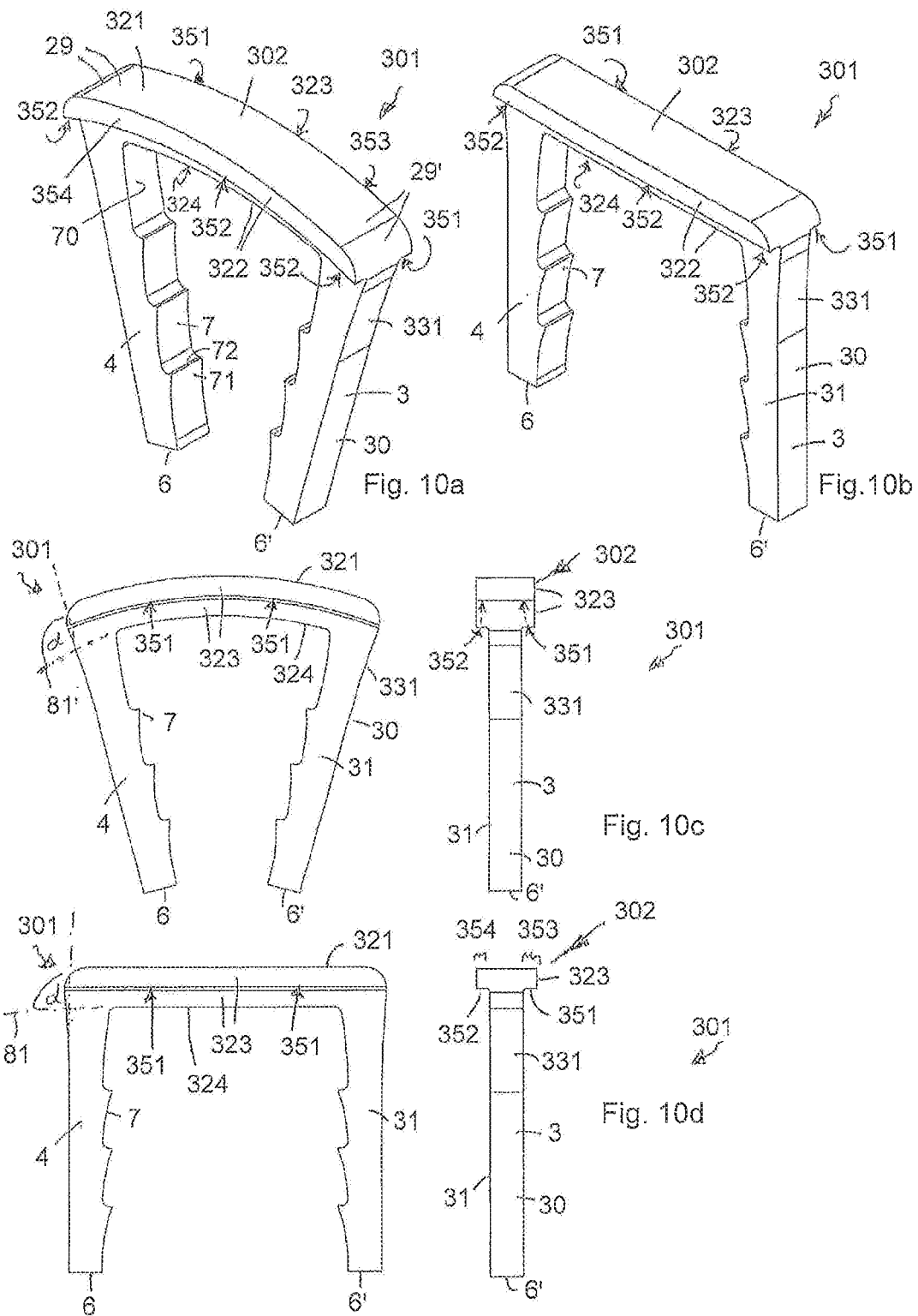

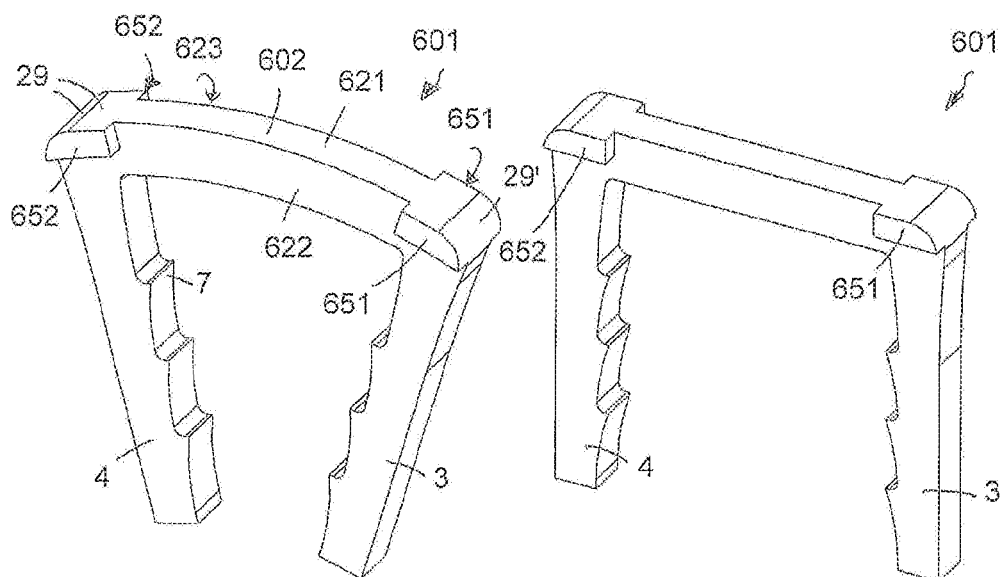
Fig. 11a
Fig. 11b
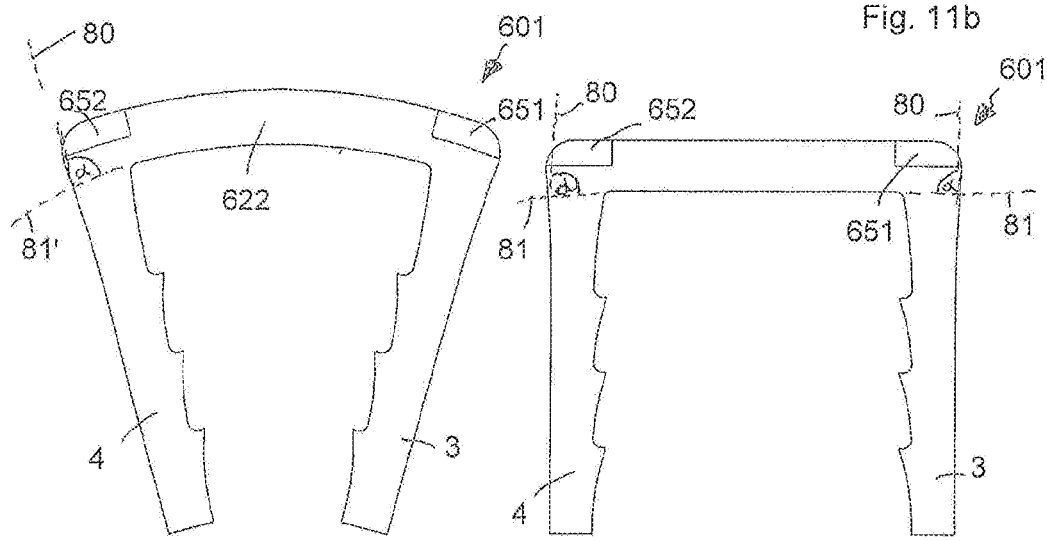
Fig. 11c
Fig. 11d

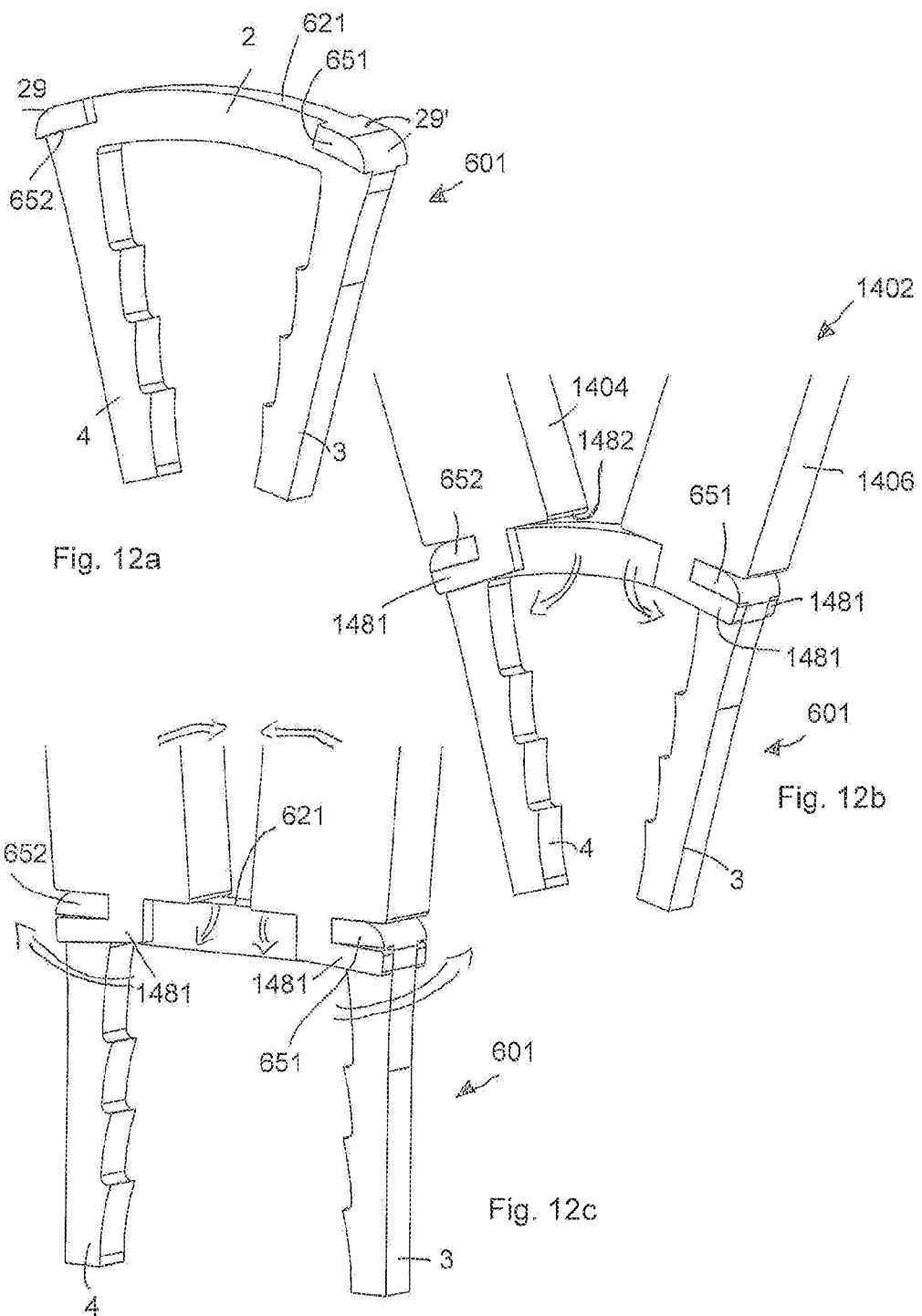

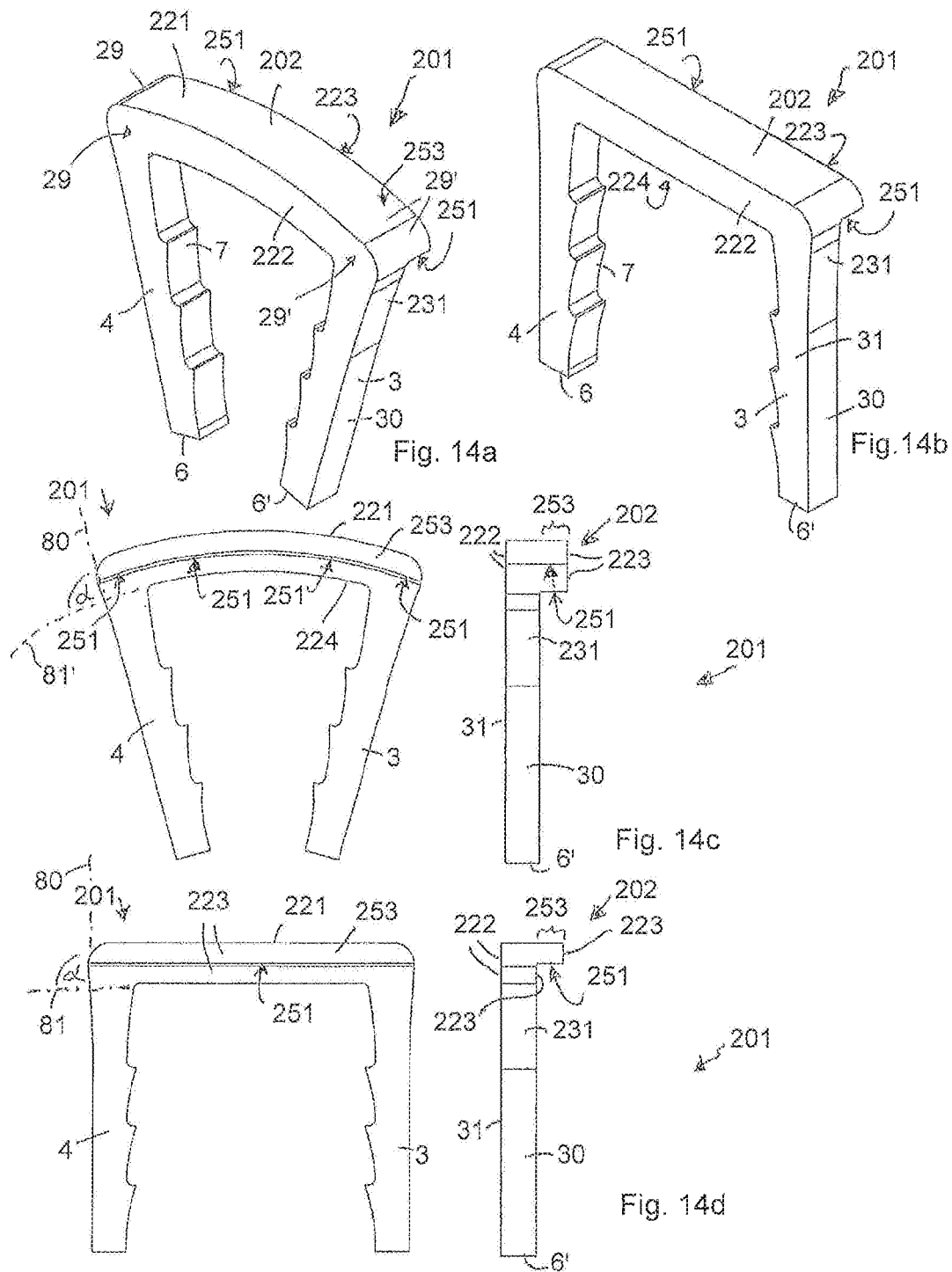

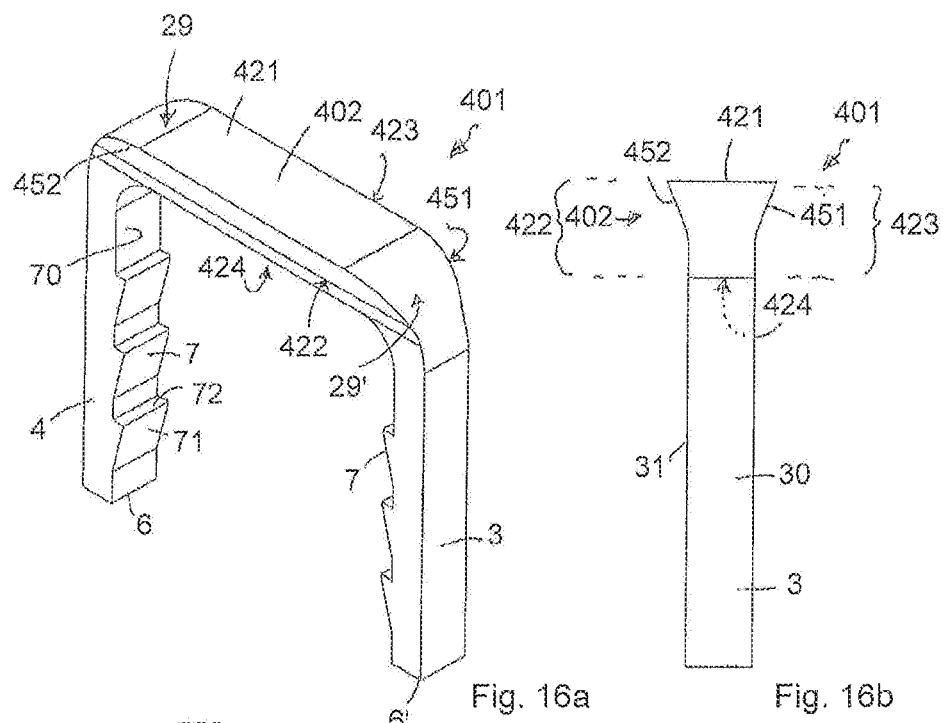
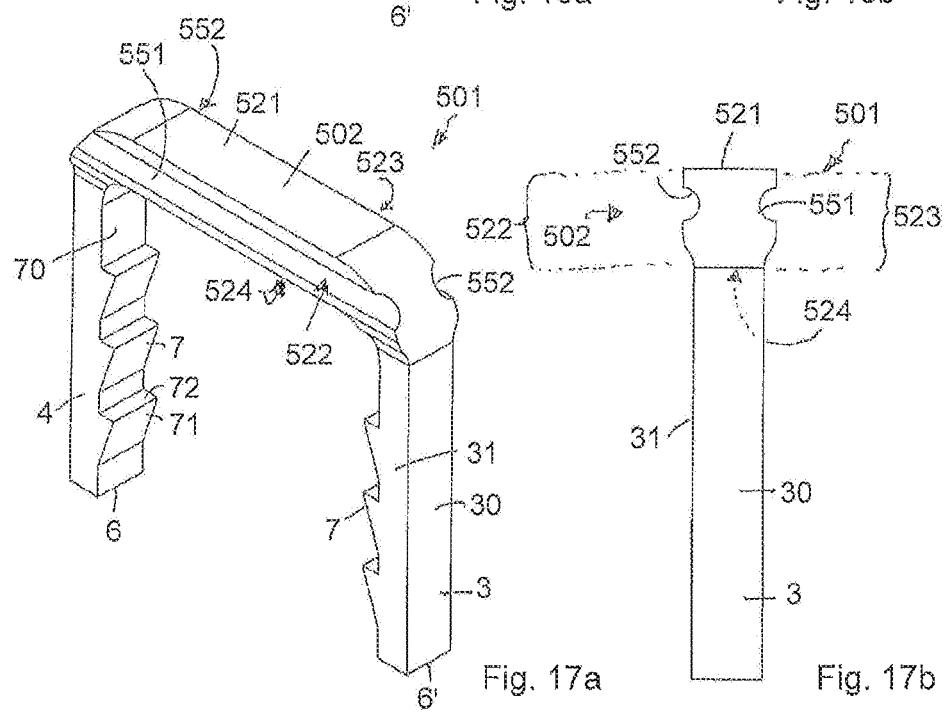

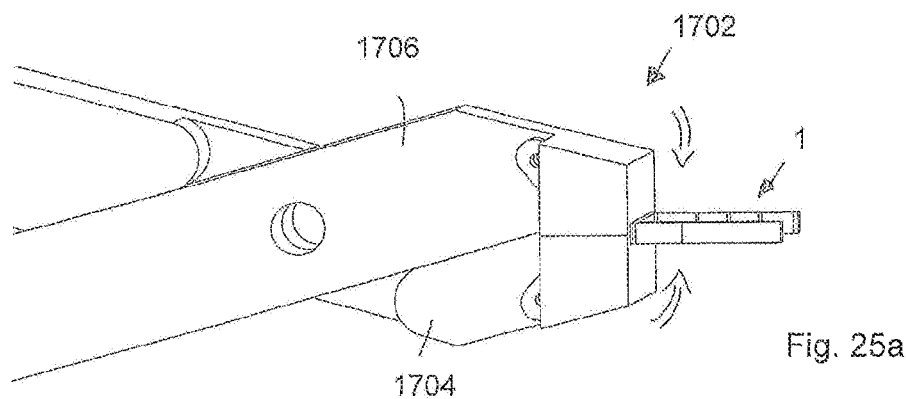
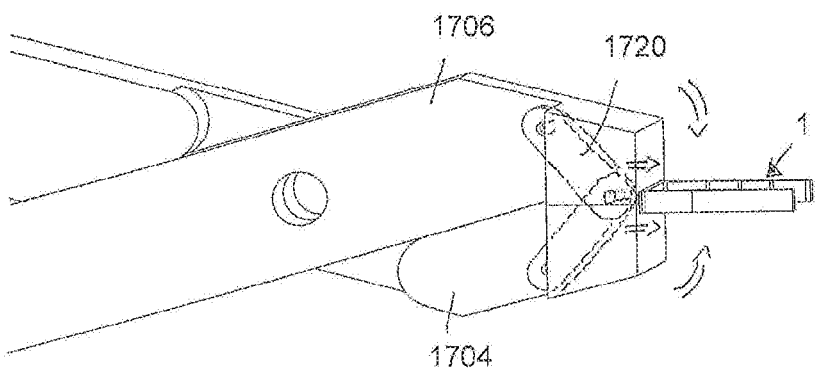
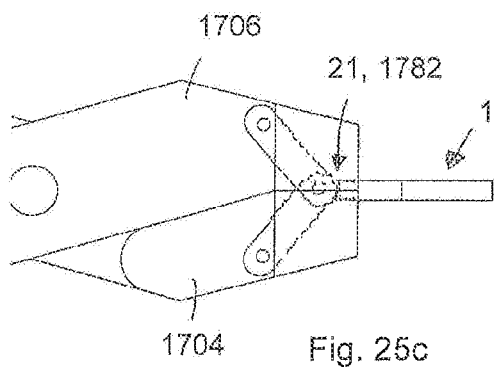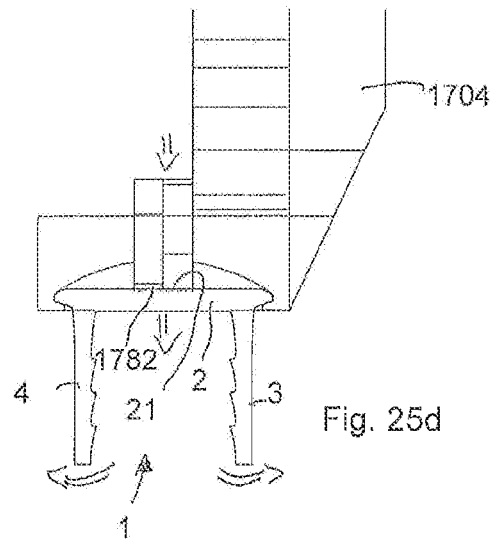

SURGICAL STAPLE AND INSTRUMENT FOR HOLDING AND IMPLANTING THE SURGICAL STAPLE

CROSS-REFERENCE TO RELATED APPLICATION(S)

The present application is a continuation of U.S. Ser. No. 16/134,111, filed Sep. 18, 2018, which is a continuation of U.S. Ser. No. 15/161,124, filed May 20, 2016, now issued as U.S. Pat. No. 10,105,134, which claims benefit of U.S. Provisional Patent Application Ser. No. 62/164,402, filed on May 20, 2015, and which claims priority from European Patent Application EP 15168542.7, filed on May 20, 2015, the contents of all of which are hereby incorporated by reference in their entireties.

BACKGROUND

Field

The present invention relates generally to surgical staples used for compressing bones or bone fragments. More specifically, the invention relates to surgical staples including a first leg for anchoring in a first bone or bone fragment, a second leg for anchoring in a second bone or bone fragment, and a bridge connecting the first leg and the second leg. The invention also relates to an instrument for holding and implanting surgical staples.

Description of Related Art

Surgical staples are used to treat angular deformations, fractures particularly with respect to the extremities, subluxation, dislocation, arthritis, or other issues that may occur with regard to bones of the human body. The staples are attached to respective bones or bone fragments to fuse the bones or bone fragments together while exerting a compressive force on them. Staples are advantageous over other fusion techniques such as plates, for example, in view of their compactness and flexibility.

Document U.S. Pat. No. 6,908,467 B2 discloses a distraction device made from a nitinol wire which includes an S-curve and bent end regions provided with hooks for anchoring in the bony material. When the distraction device is implanted, a rise of the temperature above the transfer temperature causes the shape memory material to change from a martensite state to an austenite state. The device is distracted when the S-curve assumes an elongated shape in the austenite state. The hooks self-lock in the opposing bone surfaces and the bone sections distract. Due to the superelastic characteristics of Nitinol, the distraction force remains more constant.

Document U.S. Pat. No. 7,618,441 B2 discloses a bone staple which may be made of Nitinol. The staple has a bridge and legs extending from corner joints adjacent respective end portions of the bridge. The bridge may be slightly arc-shaped whereas the legs extend parallel to each other. The bridge also slightly extends beyond the corner joints thereby forming stop means or shoulders. The shoulders serve for reinforcing the connection between the legs and the bridge, and, since the level of the shoulder is lower than the bridge, for preventing the bridges from entering into contact with the bone. The staple is used to address convexity or concaveness of the vertebral column, wherein the shape memory effect of Nitinol is employed to splay the legs of the staple inserted into respective vertebrae away from each other.

Document GB 2471648 B discloses a staple for bones. The staple may be made of a shape memory material such as NiTi and has a connector including a ring of curved portions allowed to be distracted and further including three or four legs arranged parallel to each other.

Document US 2013/0026206 A1 discloses a bone staple which has a bridge connecting two legs and which is made from Nitinol. The bridge has an S-shape in a plane perpendicular to that of the legs and the legs are inclined toward each other in a closed configuration. In an opened configuration, the legs become parallel.

Document US 2013/0231667 A1 discloses a surgical staple having a middle section or bridge and side sections or legs which cantilever from ends of the middle section at an angle close to 90°. In a relaxed configuration, the middle section is curved within the plane of the side sections and has an angle of curvature between 15° and 35°. The side sections extend towards each other in this configuration. Use of Nitinol superelastic material is also disclosed therein.

Document US 2014/0277516 A1 discloses a bone staple including a bridge and legs extending from ends of the bridge. The bridge has a straight shape in a relaxed as well as in a splayed configuration of the legs. To splay the legs, the staple is put on a storage block and two tips of respective pivoting inserter handles force the side legs into the splayed configuration at 90° relative to the bridge. The staple is made from a super elastic and shape memory material such as Nitinol ASTM 2063.

Document US 2014/0358187 A1 discloses a surgical staple and a staple insertion device. The staple may be made of Nitinol and has a bridge and legs extending from ends of the bridge. To achieve a tensioned configuration in which the legs are parallel to each other, the staple is loaded to jaws of the insertion device which may be rotated outwards by means of a spacer configured to separate the jaws, which adversely engage the legs of the staple.

SUMMARY

It is an object of the invention to provide a surgical staple and an insertion holder which improves the process of insertion of the staple into bones.

According to an embodiment, a surgical staple for compressing bones or bone fragments includes a first leg and a second leg for anchoring in respective bones or bone fragments. A bridge connects the first leg and the second leg. The bridge has a first end section and a second end section opposite the first end section. The legs extend from the respective end sections.

The bridge is provided to be arc-shaped, or curved in at least a portion thereof, in a relaxed state of the staple (e.g., a state without external forces acting on the staple). The bridge can assume a straight shape with, for example, a flat bottom surface when the staple is adjusted to an expanded, or opened, state by means of an instrument. In the expanded state of the staple, the legs are generally brought into a parallel configuration, which is suitable for insertion into pre-drilled holes in the bones or bone fragments.

The bridge may acquire mechanical energy when the staple is expanded and the bridge is bent to splay the legs towards a parallel configuration. In other words, the bridge does not only connect the legs but also contributes to achieving the expanded state of the legs. Advantageously, when the staple is in the expanded state, the bridge may attain a straight shape with its flat bottom side section, thereby closely following the surface of the bones or bone fragments involved. As a consequence, the staple may consume or take up less space within the soft tissue adjacent the bones or below the skin.

In order to allow the staple and its bridge thus expanded or bent respectively to be attached to bones or bone fragments, the surgical staple according to an embodiment further comprises at least one engagement portion for engagement by an external instrument or tool. The engagement portion allows engaging the bridge and maintaining the bridge at the straight shape. According to some embodiments of the invention, the engagement portion may be for example a recess or a projection having a surface facing or at least inclined towards one or both of the first and second legs. In many embodiments of the invention, there are at least two engagement portions provided at the bridge, which allows engaging the bridge from two sides.

The one or more engagement portions are preferably provided to extend at or adjacent the end section(s) of the bridge. This allows exertion of a pulling force onto the end sections by means of an instrument with high torque via the engagement portions, while a pressing force can be exerted on the top surface in a center section of the bridge in an opposite direction, with the consequence that the bridge bends and the legs move away from each other into a parallel configuration.

In an embodiment, the at least one engagement portion may also be located above or on a side of a plane defined by a bottom surface of the bridge opposite the legs when the bridge is straightened. Such plane may correspond to a bone surface when the surgical staple is inserted in a bone. An advantage thereby arises in that engagement structures of the external instrument may engage the at least one engagement portion at a height level above said plane, such that the legs of the staple can be inserted into pre-drilled holes in the bones or bone fragments until the flat bottom side section of the bridge abuts on the bone surface.

As a result, no parts of the external tool are sandwiched between the bridge and the bone upon attachment of the staple to the bones or bone fragments, such that it is not necessary to remove the tool before the staple is fully inserted, and then to separately hammer the staple further into the holes. Rather, the staple may be fully positioned or inserted in the bones or bone fragments using the external instrument only. Hence, the number of steps of insertion is also reduced.

According to a further embodiment, the surgical staple may at least partially be made from a shape memory material, in particular Nitinol. The surgical staple can be in its first, relaxed state upon fabrication in the austenitic phase. For easy insertion, the surgical staple can be deformed into a desired second shape having parallel legs and a straight bridge, for example, as explained above. The staple may be deformed by a transfer instrument or pliers, for example. The deformed surgical staple may be transferred from the transfer instrument or pliers to a staple holder. Another option is to use the same pliers for deformation as well as for inserting the staple into the bone(s).

When inserting the staple into bones of the human body, a so called superelasticity or pseudoelasticity of the shape-memory alloy can be utilized. This allows the staple to exert a compression onto the bones involved after insertion and release of the staple from the staple holder or pliers. The superelastic deformation of the staple from its relaxed shape to its expanded shape involves a phase transformation from austenite to martensite in the highly loaded areas of the staple. These areas remain under a certain stress after insertion of the staple, and enable the staple to exert a force onto the bones to compress the bones.

In line with the surgical staple described above, there is provided a staple holder according to a further embodiment. The staple holder includes a face formed with a cavity shaped to receive the bridge of the surgical staple in an expanded state thereof, wherein the cavity is provided with at least one engagement structure complementary to and cooperating with respective engagement portions provided at the bridge of the staple. The cavity thereby provides at least some of the reverse or opposing surface features of the bridge including the engagement portions. As the cavity is adjacent to and opens towards the face of the staple holder, the bridge may safely be received in the cavity with the legs and the bottom side section of the bridge being exposed to the outside of the staple holder, and ready for insertion into one or more bones.

According to a further embodiment, an expansion device is provided that includes a transfer portion provided on a boss, which allows displacing or moving of the surgical staple from a first portion of the boss where the staple is received in its relaxed state, to a second portion of the boss where the staple assumes the expanded state. The expansion of the staple may be an elastic deformation or a plastic deformation. An accommodation space which accommodates the staple holder is structured or positioned to allow the bridge to be received or advanced into the cavity of the staple holder when the staple is at the second portion of the boss.

BRIEF DESCRIPTION OF THE DRAWINGS

Further aspects and advantages of the invention will be better understood in view of the following description taken in conjunction with the accompanying drawings. In the drawings:

FIG. 1a shows a perspective view of a surgical staple according to a first embodiment in a relaxed state;

FIG. 1b shows a perspective view of the surgical staple according to the first embodiment in an expanded state;

FIG. 1c shows a front view of the surgical staple according to the first embodiment in the relaxed state;

FIG. 1d shows a front view of the surgical staple according to the first embodiment in an expanded state;

FIG. 2a shows a perspective view of a first embodiment of an instrument in the form of an expansion device;

FIG. 2b shows a perspective view of an expansion device according to an alternative embodiment;

FIG. 3b shows an enlarged view of a cavity of the staple holder of FIG. 3a;

FIG. 7a shows an enlarged perspective view of the staple and a portion of the pliers in FIG. 5a;

FIG. 8a shows the staple according to the first embodiment in a method of anchoring the staple in a bone;

FIG. 8b shows a step of engaging engagement portions of the staple with a third embodiment of an instrument;

FIG. 8c shows a step of expanding the staple using the third embodiment of the instrument;

FIG. 8d shows a step of aligning legs of the staple with holes previously drilled in a bone while the staple is held in an expanded state by the third embodiment of the instrument;

FIG. 8e shows a step of inserting the legs of the staple into the pre-drilled holes of the bone;

FIG. 9a shows a perspective view of a surgical staple according to a second embodiment in a relaxed state, the staple having asymmetrically extending legs;

FIG. 9b shows a perspective view of the surgical staple according to the second embodiment in an expanded state;

FIG. 9c shows a front view of the surgical staple according to the second embodiment in the relaxed state;

FIG. 9d shows a front view of the surgical staple according to the second embodiment in the expanded state;

FIG. 10a shows a perspective view of a surgical staple according to a third embodiment in a relaxed state, the staple having a bridge with a T-shaped profile and engagement portions connected on both sides of the bridge;

FIG. 10b shows a perspective view of the surgical staple according to the third embodiment in an expanded state;

FIG. 10c shows a front view and a side view of the surgical staple o according to the third embodiment in the relaxed state;

FIG. 10d shows a front view and a side view of the surgical staple according to the third embodiment in the expanded state;

FIG. 11a shows a perspective view of a surgical staple i according to a fourth embodiment in a relaxed state, the staple having a bridge with a T-shaped profile and engagement portions separated on both sides of the bridge;

FIG. 11b shows a perspective view of the surgical staple according to the fourth embodiment in an expanded state;

FIG. 11c shows a front view of the surgical staple according to the fourth embodiment in the relaxed state;

FIG. 11d shows a front view of the surgical staple according to the fourth embodiment in the expanded state;

FIG. 12a shows the surgical staple according to the fourth embodiment in a method of anchoring the staple;

FIG. 12b shows a step of engaging the staple with a fourth embodiment of an instrument;

FIG. 12c shows a step of expanding the staple using the fourth embodiment of the instrument;

FIG. 14a shows a perspective view of a surgical staple according to a sixth embodiment in a relaxed state, the staple having a bridge with an L-shaped profile;

FIG. 14b shows a perspective view of the surgical staple according to the sixth embodiment in an expanded state;

FIG. 14c shows a front view and a side view of the surgical staple according to the sixth embodiment in the relaxed state;

FIG. 14d shows a front view and a side view of the surgical staple according to the sixth embodiment in the expanded state;

FIG. 16a shows a perspective view of a surgical staple according to an eighth embodiment in an expanded state, with inclined engagement portions provided on opposite side walls of a bridge of the staple;

FIG. 16b shows a side view of the surgical staple according to the eighth embodiment in the expanded state;

FIG. 17a shows a perspective view of a surgical staple according to a ninth embodiment in an expanded state, with engagement portions formed as recesses at side walls of a bridge of the staple;

FIG. 17b shows a side view of the surgical staple according to the ninth embodiment in the expanded state;

FIG. 24c shows a partial transparent view from the side of the tip portion of the pliers of FIG. 24a;

FIG. 25a shows an enlarged perspective view of the staple and the tip portion of the pliers in a second step of the method for receiving, expanding, holding, and placing the staple in the bone, where the staple is expanded and held in the cavity at the tip portion of the pliers;

FIG. 25b shows a partial transparent view of the tip portion of the plier of FIG. 25a to show details of the toggle lever of the pliers;

FIG. 25c shows a partial transparent view from the side of the tip portion of the pliers of FIG. 25a;

FIG. 25d shows a plan view of the tip portion of the pliers, including the bottom handle, the toggle joint, and the cavity at the tip portion of the pliers;

DETAILED DESCRIPTION

Figure 3A:
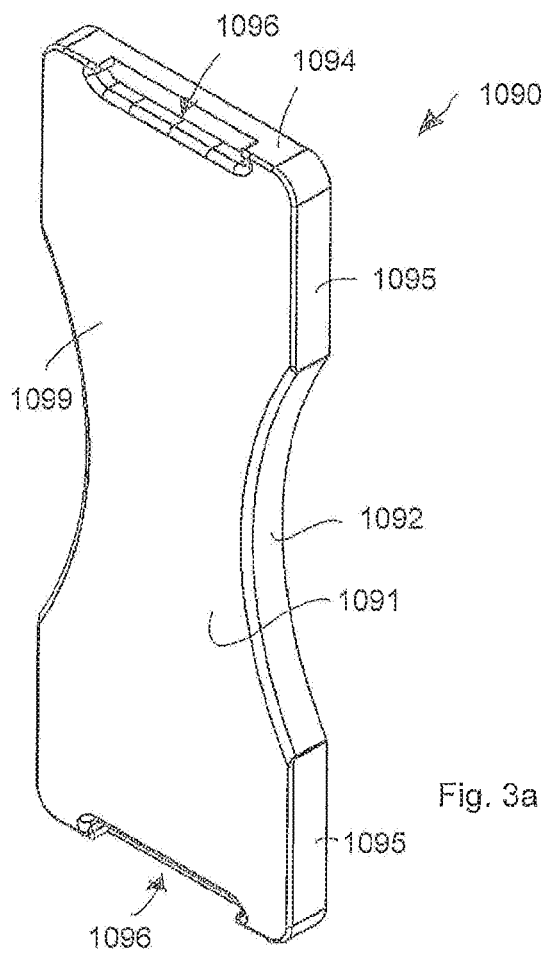
FIG. 3a shows a perspective view of a first embodiment of a staple holder.

A first embodiment of a surgical staple 1 is explained with reference to FIGS. 1a-1d. The staple 1 can be used, for example, with embodiments of an expansion device 1002 and a staple holder 1090 shown in FIGS. 2a to 4, described in greater detail below. FIGS. 1a and 1c show the surgical staple 1 in a relaxed state in perspective and front views, respectively. A relaxed state is defined herein as a state in which no external forces act on the staple. In cases where the staple is at least partially made from shape memory materials, the relaxed state further refers to an austenite phase state, corresponding to a shape of the staple that is memorized at fabrication.

The surgical staple 1 includes a bridge 2, and a first leg 3 and a second leg 4 connected to the bridge 2 at respective end sections 29, 29'. The bridge 2 includes an elongate body extending between and including end sections 29, 29'. The bridge 2 has a rectangular cross section, thereby forming a top surface 21, front and back side surfaces 22, 23 and a bottom surface 24. In the relaxed state shown in FIGS. 1a and 1c, the bridge 2 is arc-shaped or curved. The curvature, or radius of curvature, is constant in the embodiment shown, but may also vary along the length of the bridge, or may be present only in portions thereof. One example of a staple with a bridge having a variable curvature will be explained below with reference to FIGS. 18a-18d.

The legs 3 and 4 extend from the end sections 29, 29' at angles α of about 90° with respect to the bridge 2 at the location of the connections, as can be seen in FIG. 1c. The bottom surface 24 of the arc-shaped bridge 2 forms a curved plane 81' in the relaxed state, and the angles α may for example be measured at intersections of lines or planes 80 extending along lateral surfaces 30, 40 of legs 3, 4, respectively, with curved plane 81', as illustrated in FIG. 1c. As will be described in more detail below, angles α do not vary substantially when the staple 1 changes from the relaxed state to an expanded state.

In this first embodiment, as depicted in FIGS. 1a-1d, the end sections 29, 29' of the bridge 2 include extension portions 5, 5' which extend outwards beyond the locations of the connections between the bridge 2 and the legs 3, 4, respectively. The extension portions 5, 5' are both tapered and extend outwards away from the legs in a direction towards respective rounded tips, thereby forming slightly inclined surfaces which may be engaged by corresponding engagement structures of an external tool, in order to expand, or to maintain an expansion of, the surgical staple 1, as will be described below. More specifically, the extensions 5, 5' each forms an engagement portion 51, 52, which may be received, for example, in a form-fit manner by an external instrument or tool.

The legs 3 and 4 of the surgical staple 1 have outer lateral side surfaces 30 and 40, inner side surfaces 70, and front/back side surfaces 31 and 41, respectively. Each leg 3, 4 also has a rectangular cross section. At the inner side surfaces of each leg 3, 4, a number of barbs 7 are formed, each of which has a slightly inclined wall 71 and a perpendicularly protruding wall 72, forming a sharp edge. The barbs 7 are directed upwardly and serve to improve anchoring in the bone. An upper portion of the legs 3, 4 adjacent the bottom surface 24 of the bridge 2 may be left free of barbs 7. In this specific embodiment, three barbs 7 are formed at the inner surfaces 70 of the legs 3 and 4, but more or less barbs, or even no barbs, may be formed in other embodiments. Moreover, each of the legs 3, 4 has a tip 6, 6', respectively. In this embodiment, tips 6, 6' are flat surfaces which have overall square-like cross sections. However, it is also possible that the tips 6, 6' are tapered, sharp, rounded, and/or conically shaped, as known in the art, in order to improve the insertion of the legs 3, 4 into bones. This pertains also to the other embodiments described below.

The legs 3 and 4 extend substantially perpendicularly from the bridge 2 as noted above. As the bridge 2 is arc-shaped in the relaxed state, the legs 3 and 4 consequently extend towards each other. In this specific embodiment, lines or planes 80 extending along the outer lateral side walls 30, 40 of the legs, 3, 4, respectively, intersect each other at about 30° when the staple 1 is in the relaxed state. However, other intersection angles θ between 25° and 35°, or between 20° and 40°, or even angles beyond these values, are encompassed as well.

FIGS. 1b and 1d show an expanded state of the surgical staple 1 of the first embodiment. In the expanded state, the legs 3 and 4 are moved laterally away from each other, such as to be arranged in parallel with respect to each other. The expansion from the relaxed state to the expanded state is accomplished by applying mechanical energy, for example, to the bridge 2 via engaging portions 51, 52, wherein the bridge 2 may be bent like a spring. Such expansion can be performed on the staple 1 when the staple 1 is made of or includes conventional materials such as stainless steel. Such expansion can also be performed on the staple 1 when the staple 1 is made of or includes a shape memory material such as Nitinol. However, the range of deformation can be extended in such staples due to the superelasticity of the material.

Alternatively, when the staple 1 is made of or includes a shape memory material such as, for example, Nitinol, the expansion may also be accomplished by first cooling the staple 1 to effect the elastic deformation while the staple 1 is in the martensitic phase. The staple then exerts its full compression onto the bones after insertion, when the staple is again at a higher temperature (e.g., body temperature).

As can be seen particularly in FIG. 1d, the angles α that the legs 3, 4 form with the bridge 2 are maintained at 90° when the surgical staple 1 is in the expanded state. Therefore, when the legs 3, 4 are made parallel, the bridge 2 attains a straight shape, and its bottom surface 24 becomes substantially flat. The bottom surface 24 thus defines a straight plane 81 that is perpendicular to a plane defined by the bridge 2 and the legs 3 and 4.

In the expanded state shown in FIGS. 1b and 1d, the inclined surfaces of the engagement portions 51 and 52 remain above the plane 81 defined by the bottom surface 24 of the bridge 2, which may also correspond with a bone surface when the staple is implanted in or attached to bone(s). That is, when the surgical staple 1 is attached to bone, with the legs 3 and 4 inserted, for example, into holes drilled in the bone or bone fragments in advance, the staple 1 may be inserted until the bottom surface 24 of the bridge abuts on the bone surface, since the engagement portions 51 and 52, and consequently a tool attached to the engagement portions 51, 52, may remain positioned and be engaged or disengaged above the bone surface.

An embodiment of a device 1002 for expanding the surgical staple 1 is displayed in FIG. 2a. The expansion device 1002 is non-limiting, and other devices may be used to effect expansion of the surgical staple 1. The expansion device 1002 has a substantially plate-shaped body 1001, and a boss 1020, which protrudes from and is removably connected to the body 1001. A first portion 1023 of the boss 1020 adjacent a free end of the boss 1020 is arranged to receive the surgical staple 1 in a relaxed state 1101 (see FIG. 4). An upper surface 1021 of the boss 1020 is designed to contact the bridge 2, and more specifically, the bottom surface 24 thereof. Consequently, at the first portion 1023, the upper surface 1021 has a curvature corresponding to the arc-shape of the bottom surface 24 of the staple 1 or the curved plane 81' as shown in FIG. 1b. The legs 3 and 4, which extend towards each other in the relaxed state, are received in recesses 1022 formed on lateral faces of the boss 1020 below the upper surface 1021.

The boss 1020 also has a second portion 1024 adjacent to the plate-shaped body 1001. At the second portion 1024, the upper surface 1021 is almost flat, corresponding to the flatness of plane 81 of the bottom surface 24 when the staple 1 is in the expanded state, as depicted by reference 1102 in the enlarged view of FIG. 4. Also, in the second portion 1024 of the boss 1020, the depth of recesses 1022 for receiving the legs 3, 4 is decreased.

Between the first portion 1023 and the second portion 1024 of the boss 1020, there is a transfer portion 1025, where the profile of the upper surface 1021 changes or transitions smoothly from more curved to more flat, and where the depth of the recesses 1022 transitions smoothly from deeper to shallower. Hence, transfer portion 1025 allows for continuous expansion of the staple 1 by (a) attaching the staple to the boss 1020 at the first portion 1023, (b) displacing the staple 1 along the transfer portion 1025, and (c) disposing or transferring of the staple 1 at the second portion 1024 adjacent the plate-shaped body 1001, for example, to a staple holder 1090, as described below.

Figure 3B:
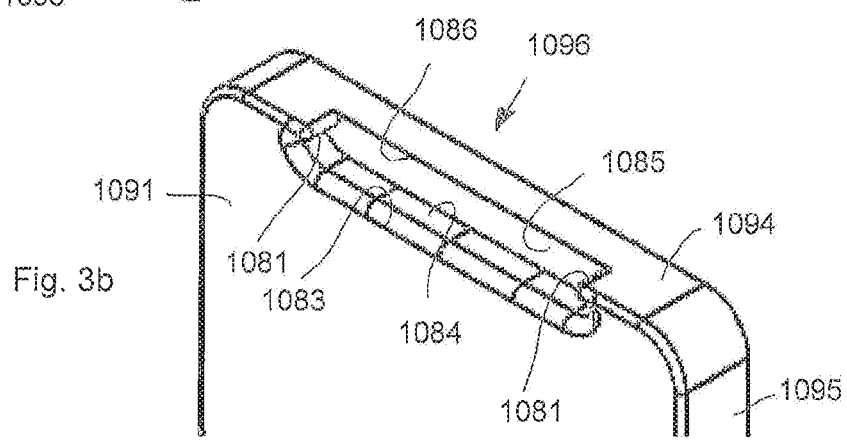

The plate-shaped body 1001 is provided with guide walls 1004 and an abutment wall 1005, which form an accommodation space 1003 for accommodating the staple holder 1090 shown in FIGS. 3a and 3b.

The staple holder 1090 has a flat, substantially rectangular plate-shaped body 1099 with opposite flat faces 1091, narrow side faces 1095, and narrow front faces 1094. Narrow side faces 1095 each has a recess 1092 configured to allow safe manual handling of the staple holder 1090. The narrow front faces 1094 respectively include apertures 1086 allowing access to cavities 1096 formed adjacent to the front faces 1094. The cavities 1096 are configured (i.e., shaped, sized, and dimensioned) to receive, for example, the bridge 2 of the staple 1 shown with respect to the first embodiment.

Moreover, the cavities 1096 are formed with engagement structures 1081, which are respectively provided at ends of cavity 1096, corresponding to the locations of the engagement portions 51, 52 of the bridge 2 when the bridge 2 is received therein. The engagement structures 1081 are in this embodiment small projections that project below the engagement portions 51, 52 of the bridge 2 when the staple 1 is held in its expanded state in the cavity 1096. Therefore, when the staple holder 1090 is positioned in the accommodation space 1003 of the expansion device 1002 and the staple 1 reaches the second portion 1024 of the boss 1020 while in the expanded state, the staple 1 is inserted into the cavity 1096 of the staple holder 1090, and the engagement portions 51 and 52 are engaged by the engagement structures 1081 to hold the staple 1 in the expanded state, as depicted by reference 1102 in FIG. 4. A counterforce is exerted onto the top surface 21 of the bridge 2, particularly in a center portion thereof, and may for example be provided by an inner back wall 1084 opposite the aperture 1086 of the cavity, which can serve as a pressing portion.

Figure 4:
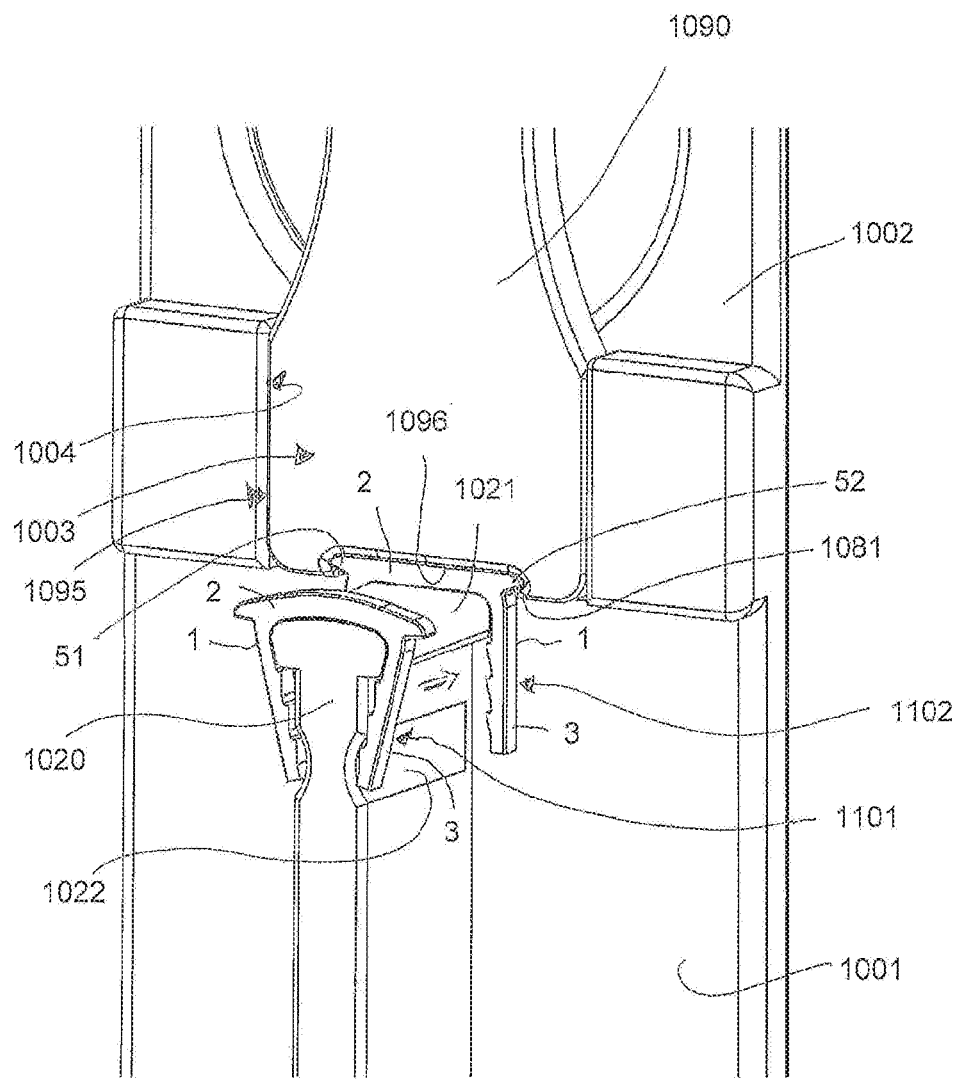
FIG. 4 shows an enlarged perspective view of a surgical staple according to the first embodiment first received in the relaxed state on the expansion device of FIG. 2a, and then received in the staple holder of FIG. 3a, which is connected to the expansion device, when the staple is adjusted to the expanded state.
Figure 5A:
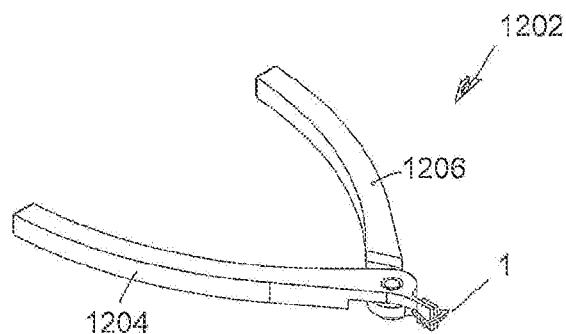
FIG. 5a shows a second embodiment of an instrument in the form of pliers receiving a staple according to the first embodiment.
Figure 5B:
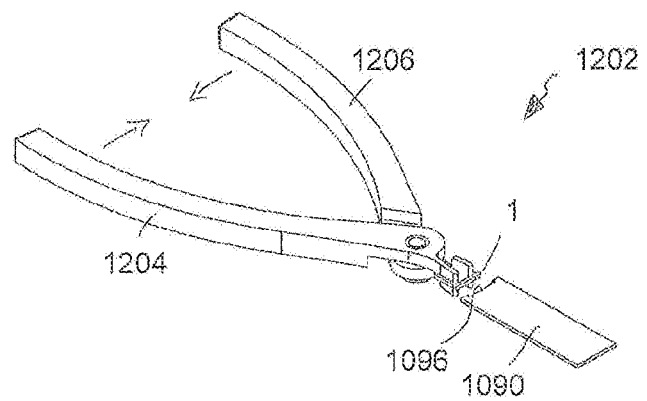
FIG. 5b shows the pliers expanding the staple according to the first embodiment.
Figure 5C:
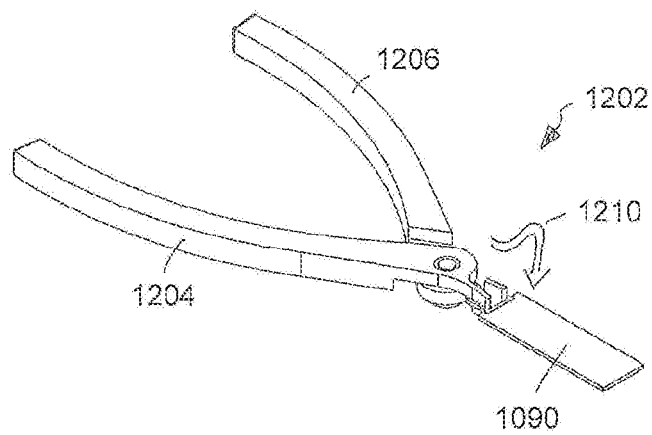
FIG. 5c shows the pliers attaching the staple according to the first embodiment to a staple holder similar to the staple holder shown in FIGS. 3a and 3b.
Figure 6A:
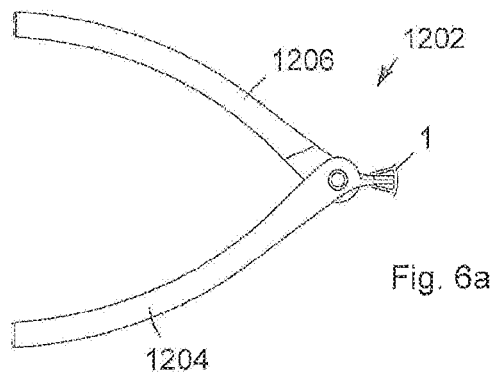
FIG. 6a shows a plan view of the pliers and staple shown in FIG. 5a, with the staple being in a relaxed state.
Figure 6B:
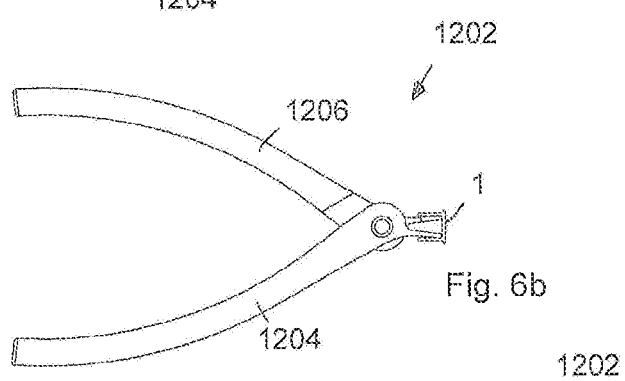
FIG. 6b shows a plan view of the pliers and staple shown in FIG. 5b, with the staple being expanded.
Figure 6C:
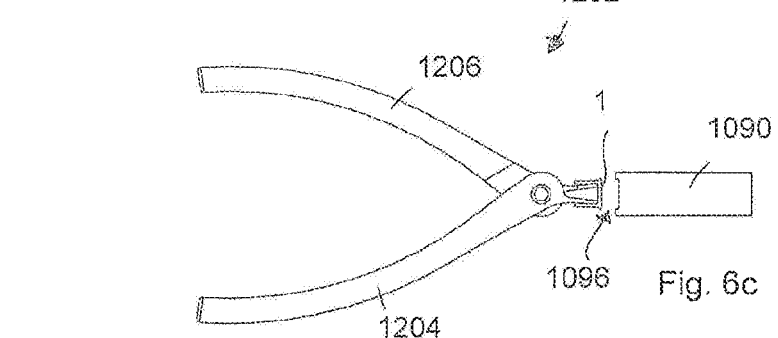
FIG. 6c shows a plan view of the pliers, staple, and staple holder shown in FIG. 5b.
Figure 6D:
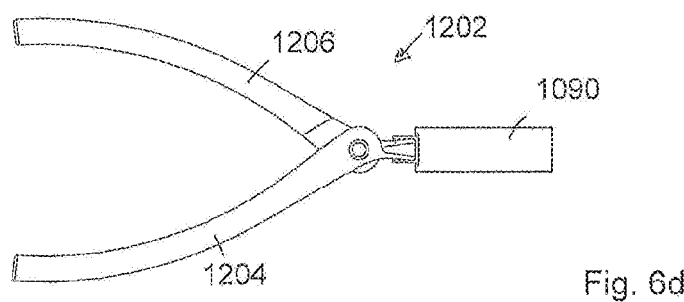
FIG. 6d shows a plan view of the pliers, staple, and staple holder shown in FIG. 5c.

As shown in FIG. 4, the accommodation space 1003 provided by guide and abutment walls 1004 and 1005 allows accommodating the staple holder 1090. A second aperture 1083 formed in one of the flat faces 1091 adjacent to the front face 1094 allows for inserting of the bridge 2 when the staple 1 is moved to the second portion 1024 of the boss 1020. When the bridge 2 is at the second portion 1024, with the legs 3, 4 abutting against the plate-shaped body 1001 of the expansion device 1002, the bridge 2 will also abut against a side wall 1085 opposite the aperture 1083 of the cavity 1096.

When the bridge 2 of the staple 1 is received in one of the cavities 1096, the boss 1020 can be removed from the body 1001, and the staple holder 1090 may be removed from the expansion device 1002, with the surgical staple 1 held in the expanded state by virtue of the engagement between engagement structures 1081 and engagement portion 51, 52, respectively, and further by virtue of a pressing force exerted by pressing portion 1084 urging the bridge 2 of the staple 1 in a direction opposite to the pulling force of the engagement structures 1081.

Next, the surgical staple 1 may be attached to a bone or bone assembly, for example, with holes pre-drilled therein (not shown in this embodiment). Since the legs 3, 4 are held by the staple holder 1090 in parallel, manual insertion of the staple 1 is facilitated until the bridge 2 abuts on the bone surface. In a next step, the staple holder 1090 may release the bridge 2 by moving the staple holder 1090 laterally relative to the staple 1, wherein the bridge 2, already adhering to the bone surface, leaves the cavity 1096 of the staple holder 1090 through the lateral second aperture 1083. As a consequence, after the bridge 2 is released, the staple 1 tries to return into its original curved shape in view of the mechanical energy stored therein, whereby a compression force is exerted by the legs 3, 4 on the engaged bones or bone fragments to compress the bones or bone fragments together.

Advantageously, no further hammering-in of the staple 1 is necessary after the staple 1 is released from the staple holder 1090, according to this embodiment and to the other embodiments described below. As a consequence, damage to the bone structure inside the pre-drilled holes in the region of the teeth may be avoided.

A further advantage of this and also of the other embodiments described herein is that, since the mechanical energy is stored in the bridge 2 when it is held at a straight shape, a distribution of the compression force of the legs 3, 4 towards each other along the legs 3, 4 is more broadly distributed, and thus improved. Furthermore, the compression force may have a maximum in a region of the first and second barbs 7 closest to the bridge 2. Moreover, the compression forces are distributed farther away from the bridge 2. For example, referring to FIG. 8h, where a staple has been inserted into holes 1351 of bone 1350, compression forces from the legs 3, 4 act upon inner walls 1352 at a deeper position of the holes 1351. Hence, the reliability of the anchoring is also considerably improved.

Figure 26:
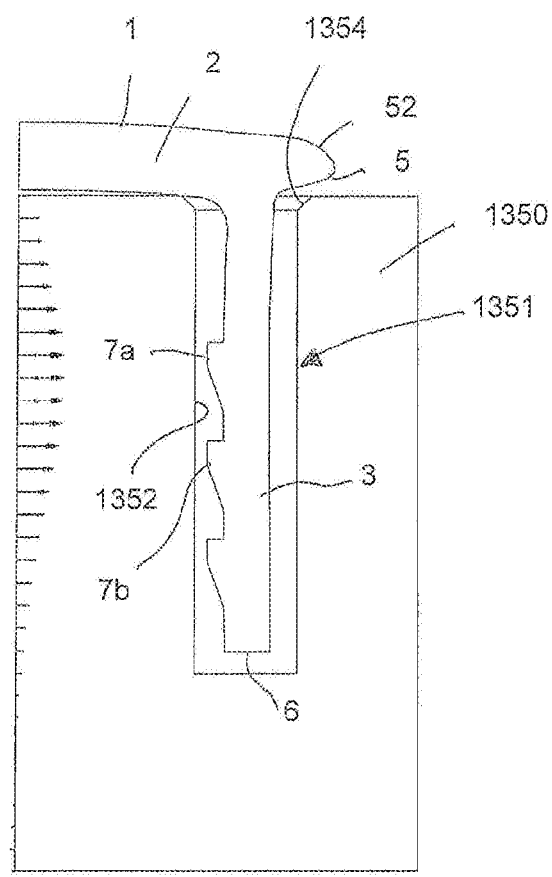
FIG. 26 is a schematic drawing showing a distribution of compression forces along a leg of a staple in an expanded state or when the staple is just released by an instrument after the staple is inserted into bone.

An impression of the distribution of compression forces exerted by the leg 3 of the surgical staple 1 is further provided in FIG. 26 as an example. The surgical staple 1 is placed in a pre-drilled hole 1351 formed in the bone 1350. The arrows indicate the amount of force exerted by respective portions of the leg 3 on the inner wall 1352 of the hole 1351 at various height levels, the forces being oriented in a direction parallel to the bridge 2 and perpendicular to the legs 3, 4, when the surgical staple 1 is in the expanded state or when the staple 1 has just been released.

As can be seen from FIG. 26, a maximum compression force is exerted at about a height level of the first barb 7a, or between the first barb 7a and the second barb 7b, while a smooth distribution of forces down to the tip 6, 6' of the leg 3 is achieved. According to the embodiments disclosed herein, a smooth maximum compressive force is achieved in a middle third or even in a bottom third of the legs of the staples. Meanwhile, in the known art, compressive forces exhibit a sharper peak at a height level of the legs that is closer to an upper surface of the bone, or closer to the bridge of the staple, in an upper third of the legs.

Still further, by storing the mechanical energy within and along the bridge, stress and strain may particularly be reduced at one of the most critical regions of the staple, the inner corner at the junction or connection between each of the legs 3, 4 and the bridge 2. This may further improve the reliability of the staple.

The above described advantages also apply to each of the other embodiments described below. One particular advantage of the first (and second) embodiment of the surgical staple is that, because the engagement portions are formed as extensions 5, 5' on an outside of legs 3, 4, the moment of torque for bending the bridge 2 is considerably increased, as compared to cases where, for example, portions of the bottom surface 24 of the bridge 2 adjacent the legs 3, 4 is engaged for expanding the staple 1. This, in turn, relaxes the requirements for the external instrument to maintain the expanded state of the staple 1.

In the above description the staple holder 1090, along with the expansion device 1002, forms a first embodiment of an expansion instrument.

Figure 7A:
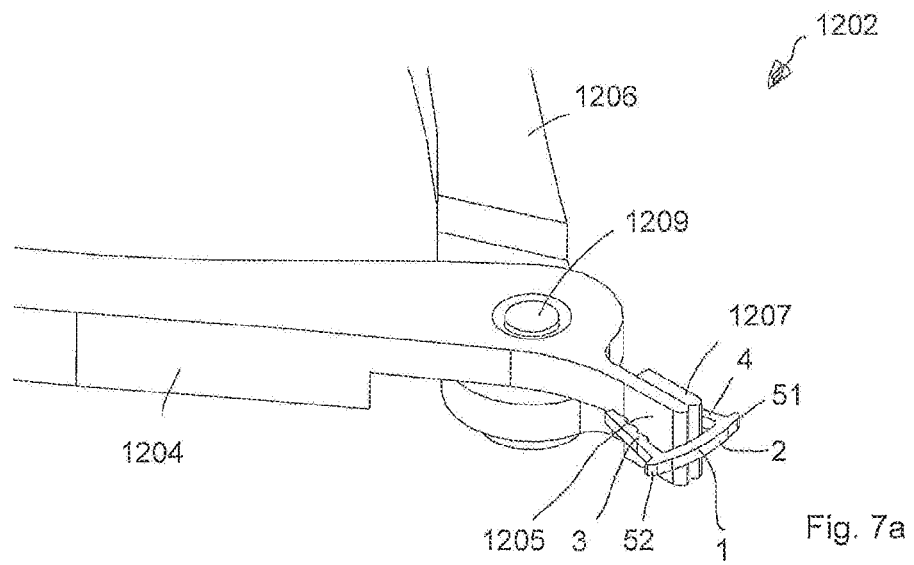
Figure 7B:
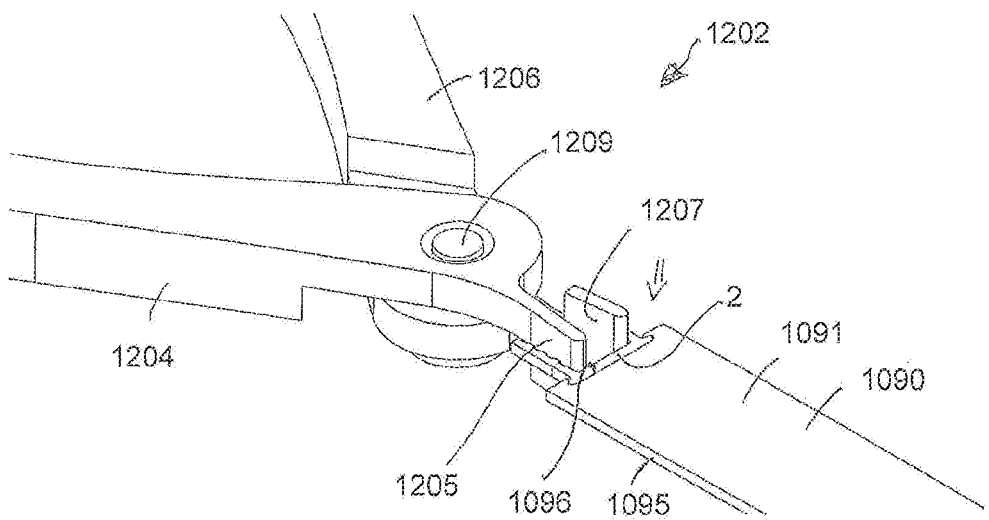
FIG. 7b shows an enlarged perspective view of the staple and portions of the pliers and staple holder in FIG. 5c.

As shown in FIGS. 5a-7b, a second embodiment of an instrument in the form of pliers 1202 is shown. The pliers 1202 can be used in conjunction with staple 1 of the first embodiment, as well as with other staples (e.g., staples 101 and 901, the embodiments of which are described in greater detail below). In this embodiment, the staple holder 1090 can be in conjunction with the pliers 1202 to receive and hold the staple 1. In the drawings of FIGS. 5a-7b, walls 1092 and 1085 of the staple holder 1090 are omitted for simplicity. The pliers 1202 include two handles 1204, 1206 rotatably coupled via shaft 1209. Each handle 1204, 1206 has a tip portion 1205, 1207, respectively. As shown in more detail in FIG. 7a, in a first position of the pliers 1202, where the handles 1202, 1204 are opened, the tip portions 1205, 1207 are correspondingly closed, such that legs 3, 4 of the staple may be received on an outer side thereof when the staple 1 is in the relaxed state. Moving the handles 1204, 1206 towards one another, to a second position of the pliers 1202, causes the tip portions 1205, 1207 to move away from each other, to splay the legs 3, 4 of the surgical staple 1 apart, as shown in FIG. 7b.

In this expanded state, the bridge 2 of the staple 1 can the be inserted into the cavity 1096 of the staple holder 1090, with the legs 3, 4 protruding from the staple holder 1090. The pliers 1202, which can be manually held under tension during this insertion step, may then be released. As a consequence, the engaging portions 51, 52 of the surgical staple 1 are forcibly engaged by the engaging structures 1081 of the staple holder 1090, and a pressing force is exerted by the pressing portion 1084 of the back wall of the cavity 1096. The pliers 1202 may then be removed or disengaged from the staple 1, and the surgical staple 1 can be placed in a bone using the staple holder 1090, similarly as described above.

A third embodiment of an instrument and a method of using the instrument is described with reference to FIGS. 8a-8h. In this embodiment, the tasks of expanding and holding the staple 1 are performed by one single device, which is different from the expansion instruments according to the first and second embodiments.

FIG. 8a shows a step of providing the surgical staple 1. Instrument 1302 may also be used in conjunction with other staples, for example, with staples 101 and 901 described in detail below.

FIG. 8b shows a step of engaging the surgical staple 1 with the third embodiment of the instrument, in the form of a pliers-type instrument 1302. The bridge 2, including the engaging portions 51, 52, of the staple 1 is received between engagement structures 1381 provided at tips of handles or arms 1304, 1306 of the instrument 1302. The handles or arms 1304, 1306, have interfaces 1305, 1307, respectively, for example, for connecting further plier mechanics or components (not shown) to allow suitable actuation of the arms 1304, 1306 by a manual input. Such mechanics are well-known in the field of pliers and serve to provide a suitable cooperating movement of the arms 1304, 1306.

FIG. 8c shows a step of the method, wherein the surgical staple 1 is expanded by moving the arms 1304, 1306 of the instrument 1302 towards one another, thereby pulling the engaging portions 51, 52 upwards, while pressing portions 1382 at the tip portions of the arms 1304, 1306, press a center portion of the top surface 21 of the bridge 2 downwards. In this state, a cavity is dynamically formed by the instrument 1302 by means of engagement structures 1381 and pressing portions 1382, which work together to hold the bridge 2 in a straight configuration and staple 1 in an expanded state.

FIG. 8d illustrates a step of applying the expanded surgical staple 1 to bone, for example, to treat a situation of hallux valgus, or a bunion. In this specific, non-limiting example, an AKIN procedure involving a surgical correction of a misalignment of the first metatarsal is performed via osteotomy. The surgical staple 1 is applied to openings 1353, 1354, for holes 1351 that may have been previously drilled into the fragments of the bone 1350 (the first metatarsal in this example). The legs 3, 4 of the staple 1 are then aligned with openings 1353, 1354, respectively, using the instrument 1302.

FIG. 8e shows a step of the method wherein the legs 3, 4 are fully inserted into the holes 1351 using the instrument 1302. The bottom surface 24 of the bridge 2 has engaged the bone surface, while the engagement structures 1381 of the instrument 1302 are still in forcible engagement with the bridge 2.

Figure 8F:
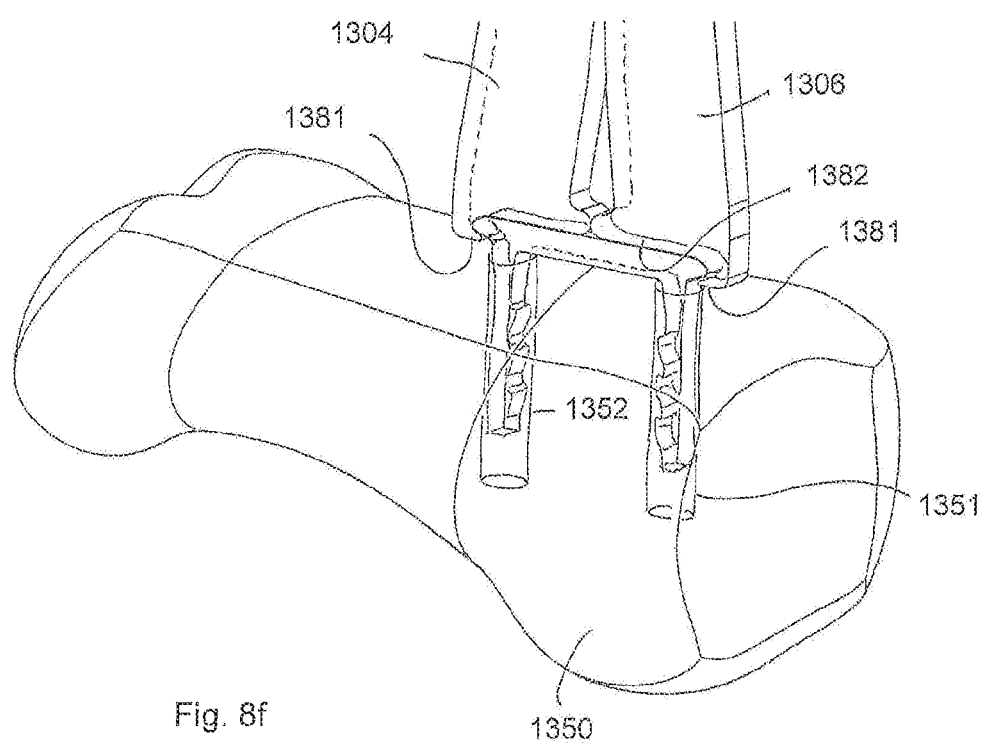
FIG. 8f shows an enlarged and partially transparent perspective view of the step depicted in FIG. 8e.

FIG. 8f shows a perspective view of the step depicted in FIG. 8e, wherein the legs 3, 4 are in the holes 1351, and are still parallel to each other while the staple 1 is held in the expanded state by the instrument 1302.

Figure 8G:
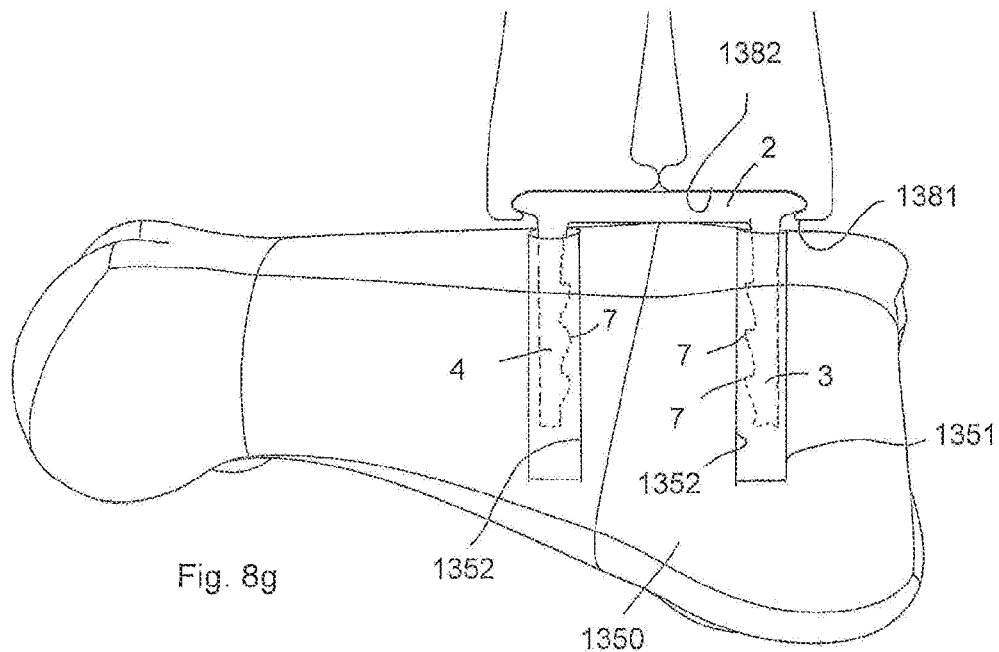
FIG. 8g shows an enlarged and partially transparent side view of the step depicted in FIG. 8e.

FIG. 8g shows a side view of the step depicted in FIGS. 8e and 8f. The legs 3, 4 have not yet engaged the side walls 1352 of the holes 1351, so the staple is thus not yet anchored in the bone 1350.

Figure 8H:
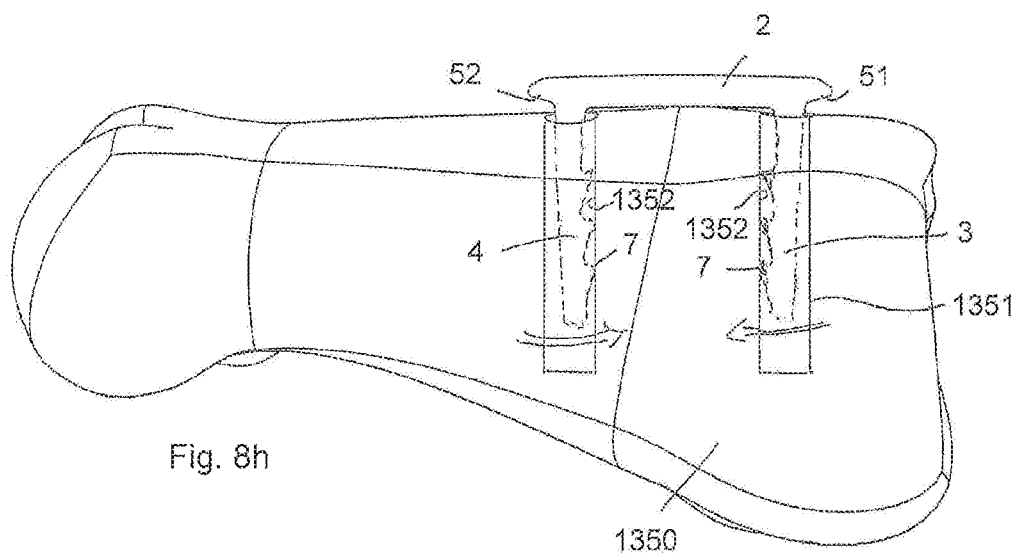
FIG. 8h shows an enlarged and partially transparent side view after a step of releasing and removing the third embodiment of the instrument from the staple.
Figures 13A, 13B:
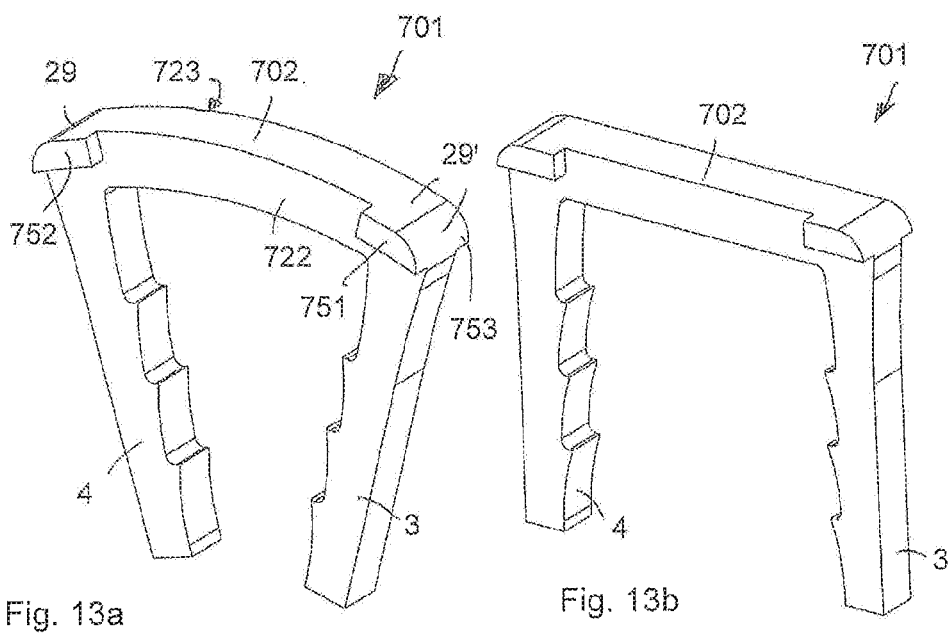
FIG. 13a shows a perspective view of a surgical staple according to a fifth embodiment in a relaxed state, the staple having a bridge with a T-shaped profile and engagement portions separated on one side of the bridge and connected on the other side of the bridge.
FIG. 13b shows a perspective view of the surgical staple according to the fifth embodiment in an expanded state.
Figures 13C, 13D:
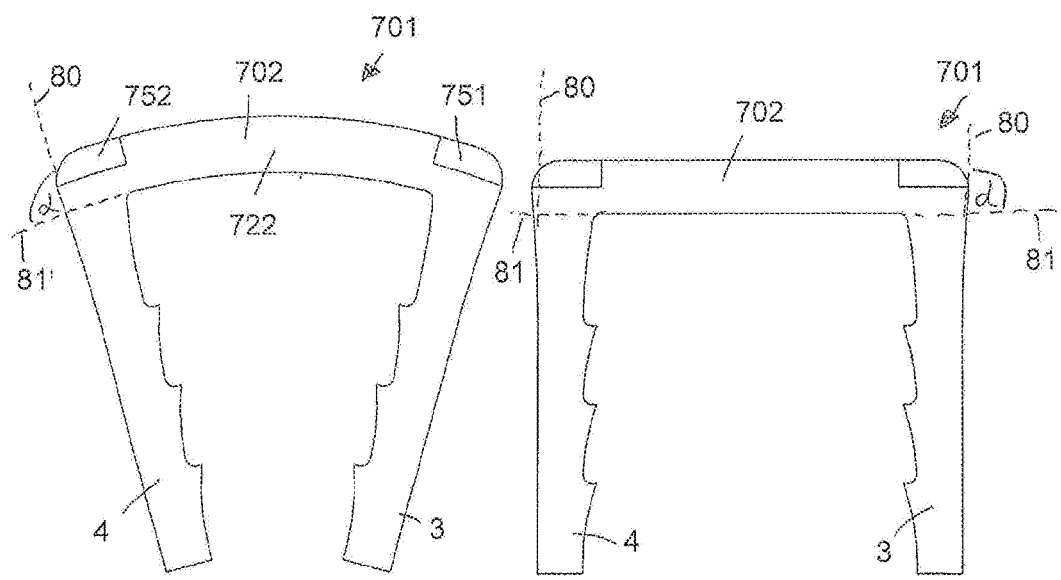
FIG. 13c shows a front view of the surgical staple according to the fifth embodiment in the relaxed state.
FIG. 13d shows a front view of the surgical staple according to the fifth embodiment in the expanded state.
Figures 15A, 15B:
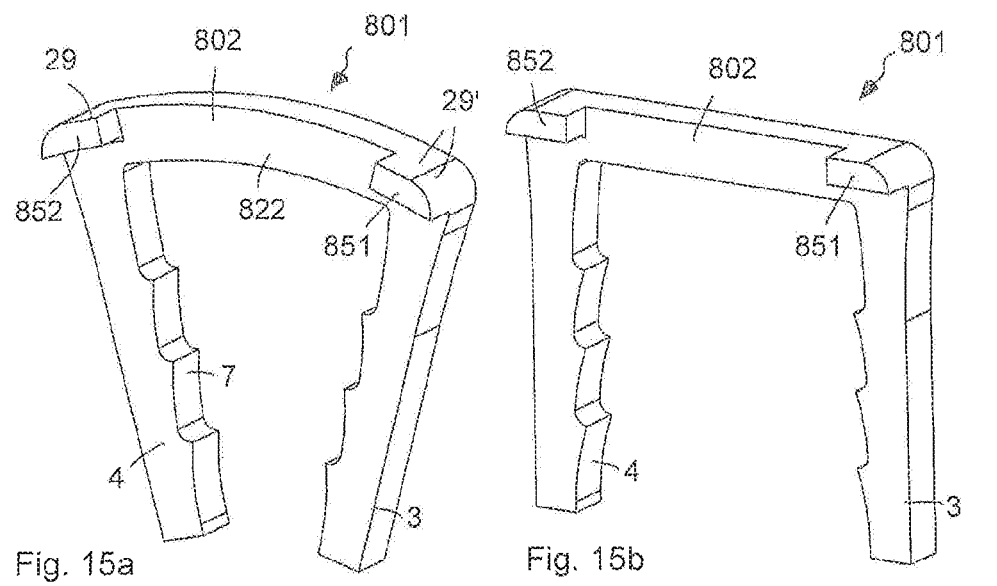
FIG. 15a shows a perspective view of a surgical staple according to a seventh embodiment in a relaxed state, the staple having a bridge with an L-shaped profile and engagement portions separated from each other on one side of the bridge.
FIG. 15b shows a perspective view of the surgical staple o according to the seventh embodiment in an expanded state.
Figures 15C, 15D:
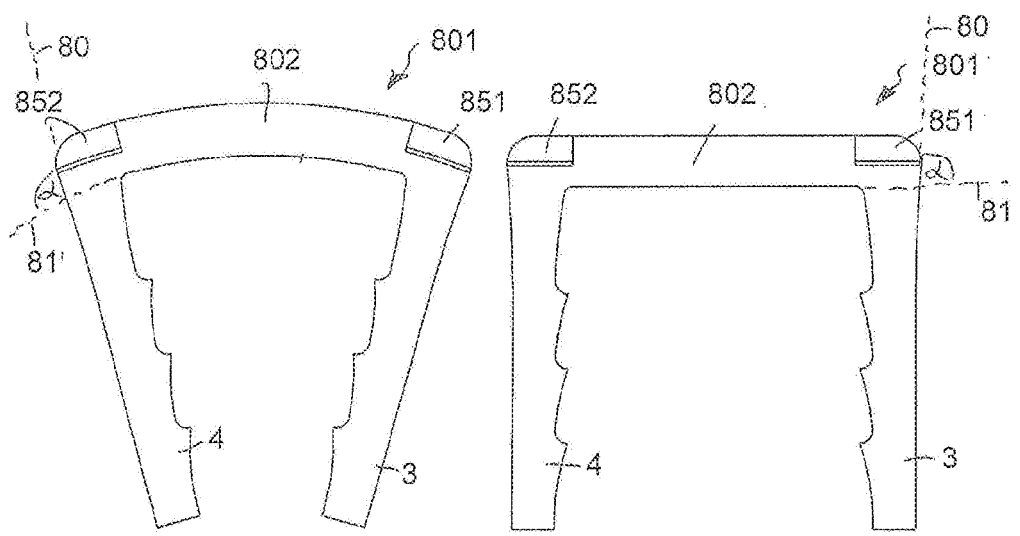
FIG. 15c shows a front and side view of the surgical staple according to the seventh embodiment in the relaxed state.
FIG. 15d shows a front and side view of the surgical staple according to the seventh embodiment in the expanded state.
Figures 18A, 18B:
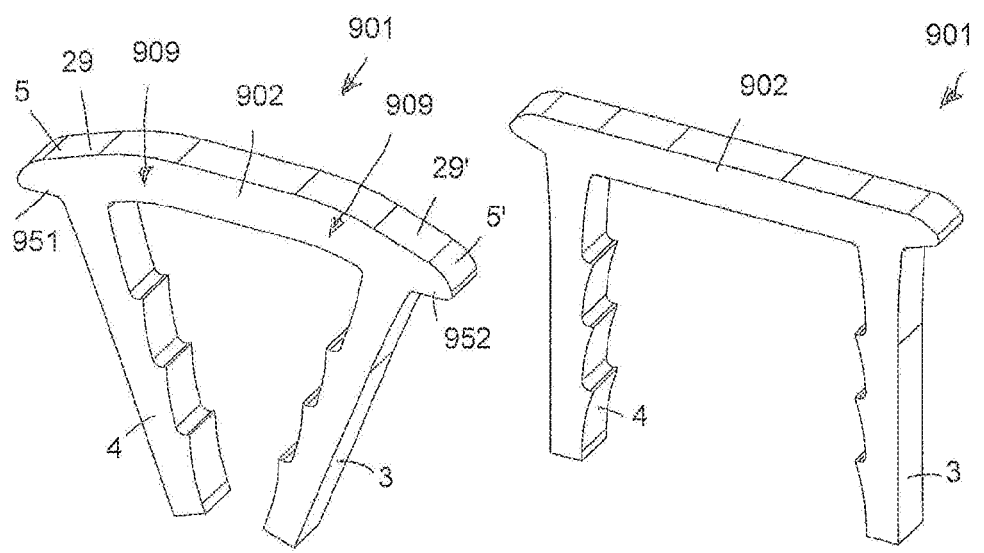
FIG. 18a shows a perspective view of a surgical staple according to a tenth embodiment in a relaxed state, the staple having a bridge with extensions and a discontinuous arc-shape.
FIG. 18b shows a perspective view of the surgical staple according to the tenth embodiment in an expanded state.
Figures 18C, 18D:
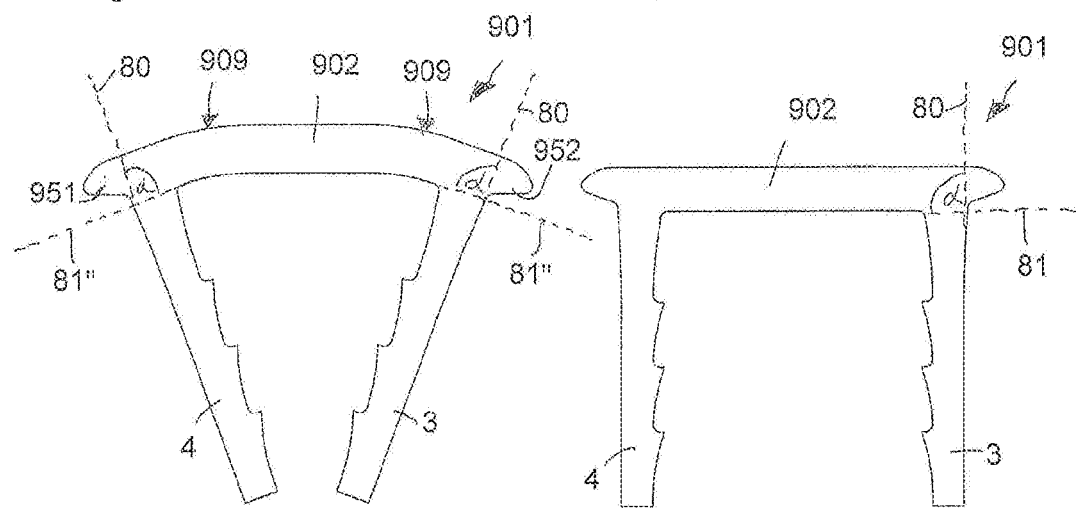
FIG. 18c shows a front view of the surgical staple according to the tenth embodiment in the relaxed state.
FIG. 18d shows a front view of the surgical staple according to the tenth embodiment in the expanded state.

FIG. 8h shows a further step of the method of implanting the staple 1 using the instrument 1302. The bridge 2 has been released by the instrument 1302. Therefore, no direct forces act on the bridge 2 to hold the staple 1 in the expanded state any more. Hence, the staple 1 begins reverting to the relaxed state and the bridge 2 starts to return back to the arc-shape. Occasionally, the legs 3, 4 abut on the mutually opposite side wall surfaces 1352 of the holes 1351, thereby compressing or urging the two bone fragments of bone 1350 towards one another. Anchoring of the staple 1 in the bone 1350 is also accomplished by the barbs 7 biting or digging into the bony side wall surfaces 1352 of the holes 1351.

A surgical staple 101 according to a second embodiment, which is a modification of the staple 1 above, will now be described with reference to FIGS. 9a-9d. Same or similar features to the staple 1 are denoted with the same reference numerals, and descriptions thereof will not be repeated.

The staple 101 of the second embodiment differs from the staple 1 of the first embodiment in that the legs 103, 104 extend from the bridge 2 at angles 13 and y, respectively, both of which are different from 90°. The legs 103, 104 therefore do not extend perpendicularly from end sections 29, 29' of the bridge 2, but rather at oblique angles. Both angles differ from 90° by about 15°, and the inclinations are oriented towards the same direction (e.g., in FIGS. 9a-9d, the legs 103, 104 are inclined towards the left). As a consequence, as can be seen in FIGS. 9b and 9d, when the staple 101 is in the expanded state, both legs 103, 104 are inclined with respect to the bridge 2, while still extending parallel to each other.

The embodiment becomes particularly advantageous in clinical situations where an inclined insertion of the surgical staple is necessary.

Further embodiments described differ from the first and second embodiments in that the engagement portions, while still being provided in or adjacent to the end sections 29, 29' of the bridge, are instead arranged on the side wall surfaces of the respective bridges. Same or similar features to those described in the first embodiment are denoted with the same reference numerals, and descriptions thereof will not be repeated.

For example, a third embodiment of a surgical staple 301 is depicted in FIGS. 10a-10d. In this embodiment, a bridge 302 is provided which has a top surface 321, a front side wall surface 322, a back side wall surface 323, and a bottom surface 324, where the orientation terms are only used for reference. As in the first and second embodiments, the bridge 302 of surgical staple 301 is arc-shaped or curved in the relaxed state shown in FIGS. 10a and 10c, and is straight or plane-shaped in the expanded state shown in the FIGS. 10b and 10d. The legs 3, 4 are arranged similarly to the staple 1 in the first embodiment. Upper ends of the legs 3, 4 adjacent the bridge 302 are slightly reinforced by inclined outer surfaces 331.

Protrusions that are flush with the top surface 321 are provided at both side wall surfaces 322, 323 of the bridge 302. Each of the protrusions extends from the first end section 29 to the second end section 29'. The protrusions represent engagement portions 351, 352, which respectively form overhangs at the side wall surfaces 322, 323 that are oriented and narrow towards the legs 3, 4, and which serve to receive a pulling force from engagement structures of an external instrument (not shown) to hold the staple 301 in an expanded state. The bridge 302 thus has a T-shape cross-section along almost its entire length.

The protrusions of the engagement portions 351, 352 extend up to the end sections 29, 29', such that an external instrument can apply the necessary moments of torque to maintain or hold the surgical staple 301 in the expanded state. For example, the staple holder 1090 of FIGS. 3a, 3b may be modified to include a cavity having engagement structures complementary in shape to the protrusions on staple 301. As was seen in the first and second embodiments, the engagement portions 351, 352 are located above a plane 81 when the staple 301 is in the expanded state, which allows removal of the external instrument from the staple 301 even when the staple 301 has been fully inserted in bone.

It should be noted that while the engagement portions 351, 352 extend from one end section 29 to the other end section 29', engagement by engagement structures of an external instrument may occur only in parts thereof, preferably at or adjacent the end sections 29, 29', as indicated above.

Accordingly, for a surgical staple 601 according to a fourth embodiment, shown with respect to FIGS. 11a-11d, engagement portions 651, 652 may be provided to extend along side wall surfaces 622, 623 only at or around end sections 29, 29'. Hence, the T-shape of bridge 602 for staple 601 is also provided only at or around the end sections 29, 29' of the bridge 602.

A fourth embodiment of an instrument 1402, illustrated with respect to FIGS. 12a-12c, may be used in conjunction with the fourth embodiment of the surgical staple 601. FIG. 12a shows the surgical staple 601 in a relaxed state, while FIG. 12b shows the instrument 1406 attached to the staple 601 in the relaxed state. The instrument 1402 may be, for example a pliers-type instrument, such as spreading pliers, or another device. The instrument 1402 may have arms or handles 1404, 1406 that are similar to the arms 1304, 1306 of the instrument 1302 in FIGS. 8b-8g.

The arms or handles 1404, 1406 have engagement structures 1481 extending from tip portions of the arms 1404, 1406, that extend outwardly from a central portion of the bridge 602 to engage around or under the engagement portions 651, 652 of the bridge 602. The handles or arms 1404, 1406 can then be moved towards one another for the tip portions to rotate relative to one another, as shown in FIG. 12c, thereby lifting or pulling the engagement portions 651, 652 with the engagement structures 1481. At the same time, flat pressing portions 1482 also provided at the tip portions of the arms or handles 1404, 1406 press onto the top surface 621 of the bridge 602, which results in an expansion of the staple 601. The further steps may then be the same as or similar to those explained with regard to FIGS. 8d-8h.

A fifth embodiment of a surgical staple 701 is shown in FIGS. 13a-13d. The surgical staple 701 differs from the staples 301 and 601 in that one side wall surface 722 of the bridge 702 has two projections corresponding to engagement portions 751, 752 provided only at the end sections 29, 29', while the other side wall surface 723 has one continuous projection corresponding to an engagement portion 753 that extends fully from one end section 29 to the other end section 29'.

A sixth embodiment of a surgical staple is depicted in FIGS. 14a-14d. In this embodiment, a bridge 202 is provided which has a top surface 221, a front wall surface 222, a back wall surface 223, and a bottom surface 224 where the orientation terms are used only for reference. As in the previous embodiments, the bridge 202 of surgical staple 201 is arc-shaped or curved in a relaxed state, as shown in FIGS. 14a and 14c, and is straight or plane-shaped in an expanded state, as shown in the FIGS. 14b and 14d. The legs 3, 4 are similar to legs 3, 4 of the staple 1 in the first embodiment. Upper ends of the legs 3, 4 adjacent to the bridge 202 are slightly reinforced by inclined outer surfaces 231.

A protrusion that is flush with the top surface 221 is provided only at the back wall surface 223, and extends along the back wall surface 223 from the first end section 29 to the second end section 29'. Similarly as seen in previous embodiments, the protrusion 253 forms an engagement portion 251, which may be engaged by an engagement structure of an external instrument (not shown) to hold the surgical staple 201 in the expanded state. The cross section of the bridge 202 of the staple 201 according to this embodiment is L-shaped.

The advantages and effects achieved by the sixth embodiment are also similar to those of the staples in the third to fifth embodiments. The surfaces of engagement portions 251 are oriented to, or face, the legs 3, 4, and are located above a plane 81 defined by the bottom surface 224 of the bridge 202 when the staple 201 is in the expanded state.

A seventh embodiment of a surgical staple 801 is shown in FIGS. 15a-15d. The surgical staple 801 is a simple modification of the staple 201 shown in the sixth embodiment, wherein the projection extends only at or around the end sections 29, 29' to yield single-sided engagement portions 851, 852, which extend along the side wall surface 822 only in a limited region.

A surgical staple 401 according to an eighth embodiment will be described with reference to FIGS. 16a-16b, where the surgical staple 401 is shown only in an expanded state. A relaxed state of the staple 401 (not shown) is analogous or similar to the relaxed states of the staples in the previous embodiments. The staple 401 is similar to the staple 301 according to the third embodiment, in that two continuous protrusions are respectively formed at side wall surfaces 422, 423 of bridge 402, and are flush with the top surface 421. However, different from the staple 301 in the third embodiment, the protrusions on staple 401 include slightly oblique surfaces, which are only slightly inclined and narrow towards the legs 3, 4. These oblique surfaces extend along the bridge 402 from the first end section 29 to the second end section 29' and are located above the plane 81 defined by the bottom surface 424 of the bridge 402 when the staple 401 is in an expanded state. The protrusions and oblique surfaces form engagement portions 451, 452, which may be engaged by corresponding engagement structures of an external instrument (not shown), to maintain or hold the staple 401 in the expanded state prior to and during implantation of the staple 401.

A ninth embodiment will be described with reference to FIGS. 17a-17b, which shows a surgical staple 501, also only in an expanded state. A relaxed state of staple 501 (not shown) is analogous or similar to the relaxed states of the staples in the previous embodiments. For staple 501, side wall surfaces 522 and 523 of bridge 502 include recesses extending from the first end section 29 to the second end section 29' at a central height level of the side wall surfaces 522, where the recesses are also above a plane 81 defined by bottom surface 524 of the bridge 502 when the staple 501 is in an expanded state. The recesses have concave cross sections and form engagement portions 551, 552 to be engaged by engagement structures of an external instrument (not shown), for maintaining or holding the surgical staple 501 in the expanded state. Since the recesses reduce the thickness of the bridge 502, the overall layout of the bridge 502 can be provided with a correspondingly larger thickness to comply with stability requirements of the surgical staple 501.

This staple embodiment provides an advantageous alternative to the previously described staples, since corresponding engagement structures of an external instrument may have a complementary shape, for example, elongate convex protrusions, and no further contact with the top surface 521 of the bridge 502 may be necessary to maintain or hold the staple 501 in the expanded state. This embodiment may therefore be particularly useful when pliers or the like are used as the external instrument to hold and implant the staple.

Several other modifications may also be made with regard to the above embodiments.

For example, in the above embodiments, the cross section of the bridge and the legs for some of the staple embodiments was described to be rectangular. Alternatively, the cross sections may be, for example, circular, oval, or polygonal, and may include, for example, rounded or chamfered edges.

In addition, in the above embodiments, when the staples are in a relaxed state, the arc-shapes of the bridges of the staples were generally described to be continuous and smooth. However, it is also possible that only portions of the bridge are curved or bended. A tenth embodiment of a surgical staple 901 is illustrated in FIGS. 18*a*-18*d*. The bridge 902 includes two bending portions 909 which connect straight portions of the bridge 902. The bending portions 909 are provided adjacent to or on both sides of a center portion of the bridge 902, but not at the end sections 29, 29'. The surgical staple has projecting extensions 5, 5' forming engagement portions 951, 952, such that the same or similar advantages and effects described with regard to the first embodiment of the surgical staple 1 may also be achieved here.

Moreover, in the above embodiments, Nitinol was described as one of the materials from which the surgical staple is made, or at least partially made. Alternatively, in embodiments where staples include shape memory, any suitable shape memory material may be employed. Also, non-shape memory materials are encompassed by the invention. Further examples are biocompatible materials including stainless steel, titanium, beta-titanium alloys including molybdenum, vanadium, niobium, tantalum, zirconium, manganese, iron, chromium, cobalt, nickel, and copper. Titanium alloys also provide excellent formability and reliability. In addition, magnesium based materials, for example, may also be used.

In the above embodiments, the staples include a bridge and two legs generally extending within one plane. However, more complex three-dimensional structures are encompassed as well. Moreover, staples with more than two legs may also be used.

Furthermore, in the above embodiments, the bridge of the staple is described to attain a straight flat shape when the staple is in the expanded state. However, other bridge shapes may also be attained in the expanded state, when the legs are arranged in parallel and ready for insertion into bone.

In the above third embodiment for example, a surgical staple 301 including engagement portions 351, 352 formed as projections extending along the outer side wall surfaces 322, 323 is described. The projections are formed such as to extend above a plane defined by the bottom surface 324 of the bridge 302 when the staple 301 is in the expanded state. In other words, the engagement portions 351, 352 are entirely distant or spaced apart from the bottom surface 324 in the staple 302, as well as in staples described with respect to the other embodiments.

Figures 20A, 20B:
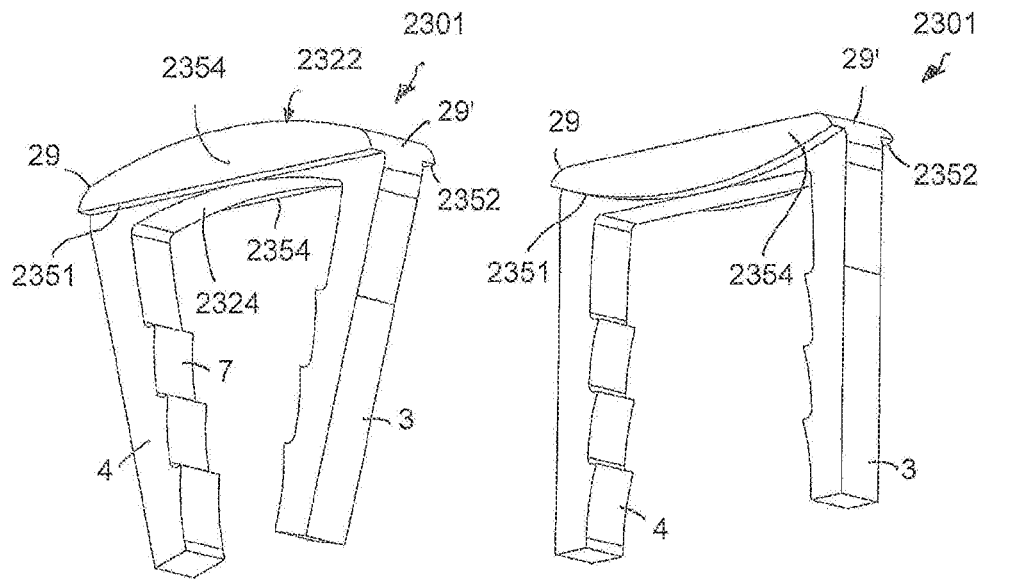
FIG. 20a shows a perspective view of a surgical staple according to an eleventh embodiment in a relaxed state, the staple having a bridge with a T-shaped profile and a convex-shaped engagement portion.
FIG. 20b shows a perspective view of the surgical staple according to the eleventh embodiment in an expanded state.
Figures 20C, 20D:
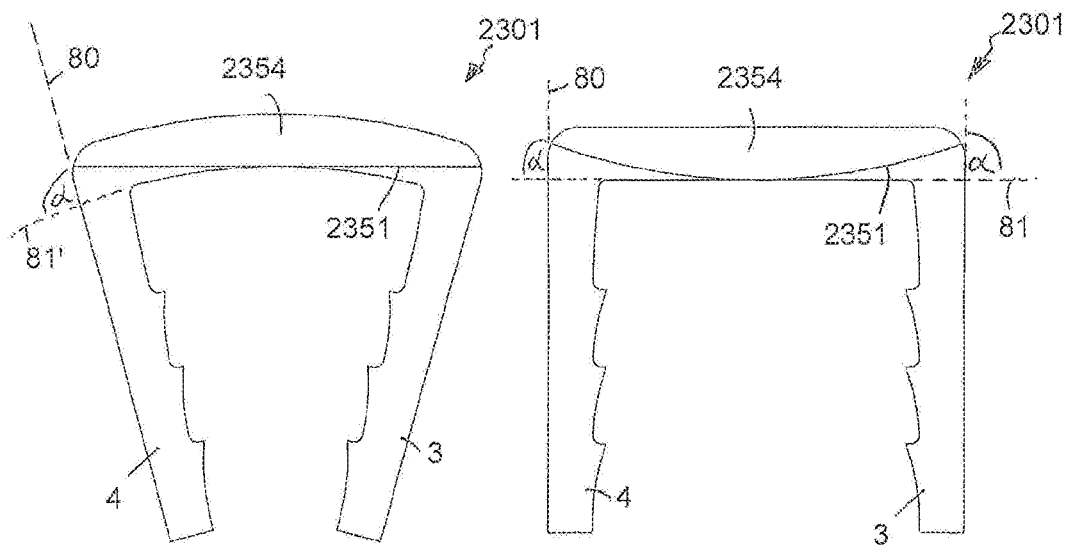
FIG. 20c shows a front view of the surgical staple according to the eleventh embodiment in the relaxed state.
FIG. 20d shows a front view of the surgical staple according to the eleventh embodiment in the expanded state.

However, in yet another, eleventh, embodiment shown in FIGS. 20*a*-20*d*, a surgical staple 2301 has a bridge 2302 including a bottom surface 2324 and one or more projections 2354 with engagement portions 2351, 2352, where the bottom surface 2324 and the engagement portions 2351, 2352 approach each other at a center portion of the bridge 2302. Bottom surfaces of the engagement portions 2351, 2352 can assume, for example, a straight shape while the bottom surface 2324 of the bridge 2302 is curved, when the staple 2301 is in the relaxed state, as seen in FIGS. 20*a* and 20*c*. Meanwhile, the bottom surfaces of the engagement portions 2351, 2352 can assume a convex shape, while the bottom surface 2324 of the bridge 2302 straightens, when the staple 2301 is in the expanded state, as shown in FIGS. 20*b* and 20*d*.

Nevertheless, similarly as explained with respect to the embodiment of FIG. 12*b*, for example, the parts of the projections which are configured for engagement by an external tool for expansion of the staple, are in some embodiments, ideally provided at or adjacent the end portions 29, 29' of the staple, so that sufficient torque can be applied to the staple for the expansion. In this regard, even in this embodiment, the outer regions of the engagement portions 2351, 2352 that engage an external tool may still extend at least partially above a plane defined by a bottom surface 2324 of the bridge 2302 when the staple is in the expanded state, to achieve safe placement of the staple 2301 in bone. As a consequence of the convex arc-shape of the bottom surface of the projection 2354, the bottom surface is inclined with respect to the legs 3, 4, as well as with respect to the plane 81 defined by the bottom wall surface 2324 of the bridge 2302 when the staple 2301 is in the expanded state, similarly as described with respect to the first embodiment.

Figure 19A:
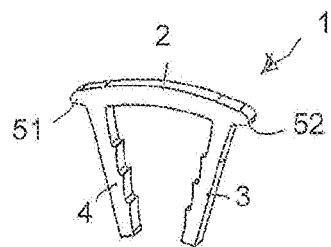
FIG. 19a shows a staple according to the first embodiment in a method for anchoring the staple.

Meanwhile, in the above instrument embodiments, tip portions provided at arms or handles of various plier-type instruments are described to form cavities for receiving and holding bridges of staples. However, it also possible in other tool or instrument embodiments that further parts also contribute to the shape of the cavity, for example, as seen in a fifth embodiment of an instrument 1502, explained with respect to method steps in FIGS. 19*a*-19*c*. A surgical staple 1 is provided in FIG. 19*a*, with engagement portions 51, 52 formed as extensions 5, 5' of a bridge 2, similarly as seen in FIGS. 1*a*-1*d*.

Figure 19B:
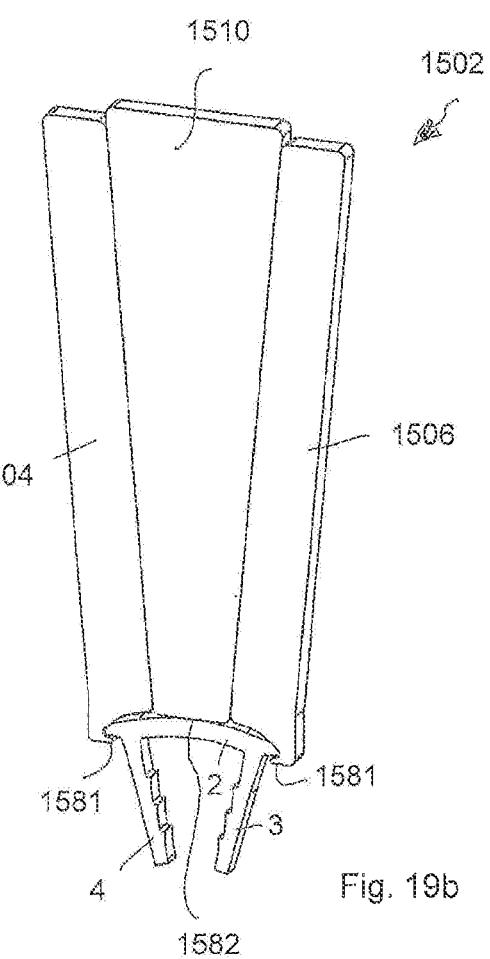
FIG. 19b shows a step of using a fifth embodiment of an instrument to receive the staple when the staple is in a relaxed state.

The instrument 1502, which may be a pliers-type instrument, has handles or arms 1504, 1506, with tip portions similar to those described with respect to the embodiments of instruments 1302, 1402 described above. Engagement structures 1581 are provided to engage the engagement portions 51, 52 of the bridge 2, as shown in FIG. 19*b*.

For instrument 1502, an additional pressing member 1510 is further provided between arms or handles 1504, 1506. Pressing member 1510 has a tapered profile, such that when advanced towards a top surface of the bridge 2, the arms or handles 1504, 1506 may be slightly displaced away from each other. When a pressing portion 1582 at a front end of the pressing member 1510 abuts the top surface of the bridge 2, the bridge 2 is bent, and a length between the end sections 29, 29' or extensions 5, 5' along a horizontal or width direction of the staple 1 increases.

Figure 19C:
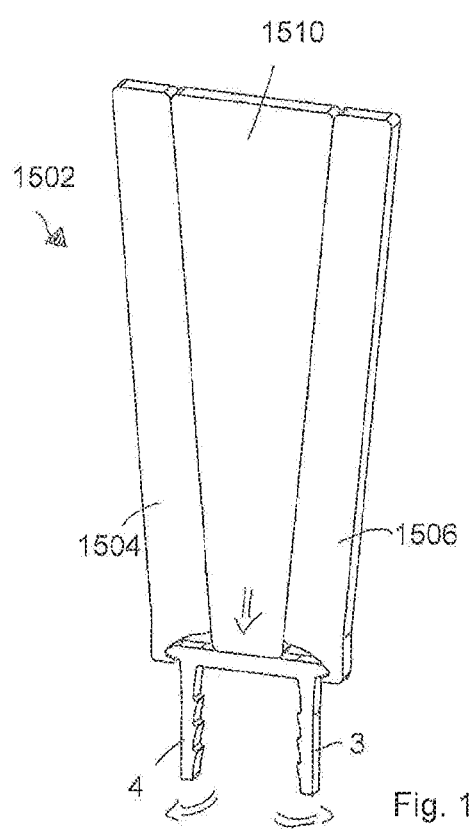
FIG. 19c shows a step of expanding the staple using a pressing member of the fifth embodiment of the instrument.

However, as shown in FIG. 19*c*, when the staple 1 is expanded, the taper of pressing member 1510 also allows the arms 1504, 1506 to also further separate, so that the cavity formed by the arms 1504, 1506 is also slightly elongated to form a complementary shape providing a form-fit connection for the bridge 2.

Figure 21:
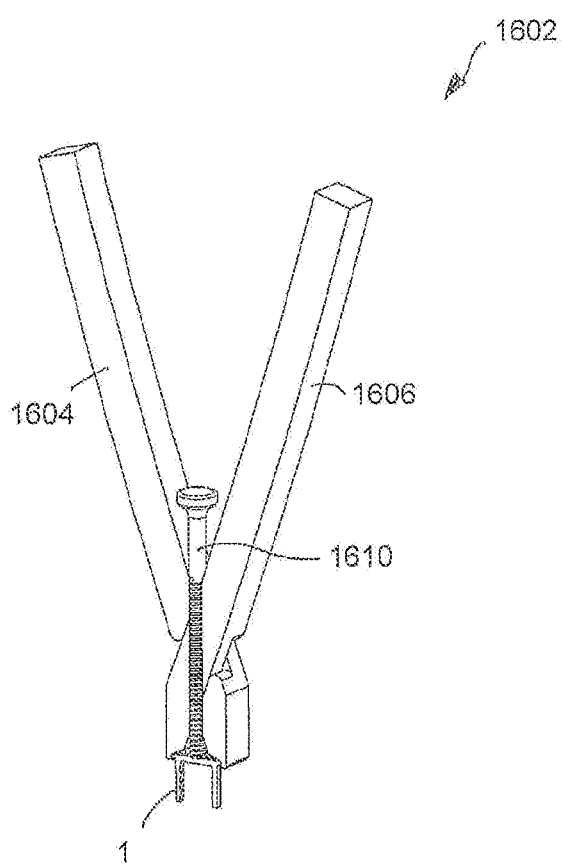
FIG. 21 shows a perspective view of a sixth embodiment of an instrument in the form of pliers, in a state of holding an expanded staple of the first embodiment, the pliers having an inner screw member to maintain the expanded state of the staple.
Figure 22A:
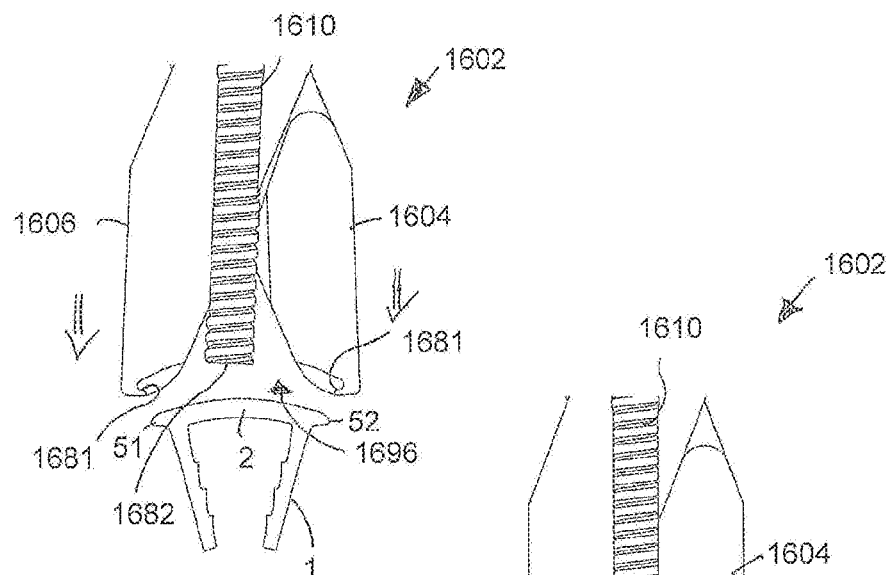
FIG. 22a shows an enlarged view of tip portions of the pliers of FIG. 21 in a first step of a method for receiving, expanding, holding, and placing the surgical staple in a bone.
Figure 22B:
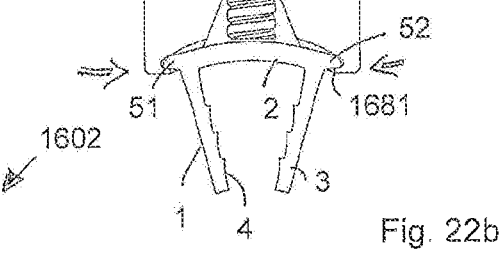
FIG. 22b shows the pliers and staple of FIG. 22a in a second step of the method.
Figure 22C:
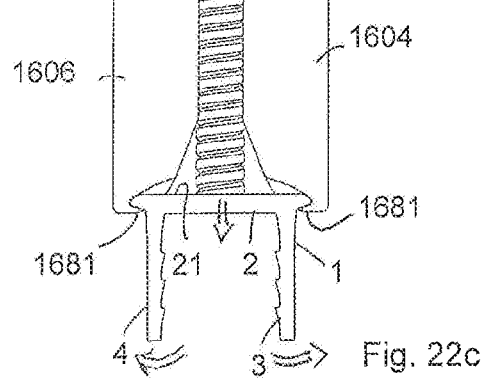
FIG. 22c shows the pliers and staple of FIGS. 22a and 22b in a third step of the method.
Figure 23A:
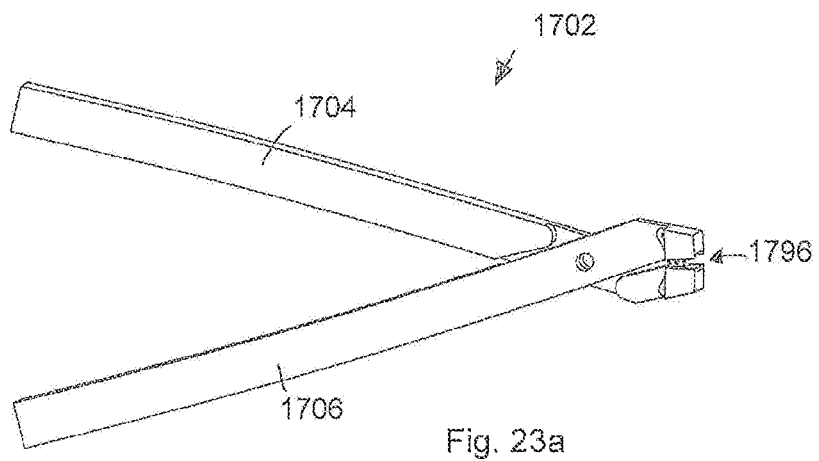
FIG. 23a shows a perspective view of a seventh embodiment of an instrument in the form of pliers, in an opened state, the pliers having a toggle lever.
Figure 23B:
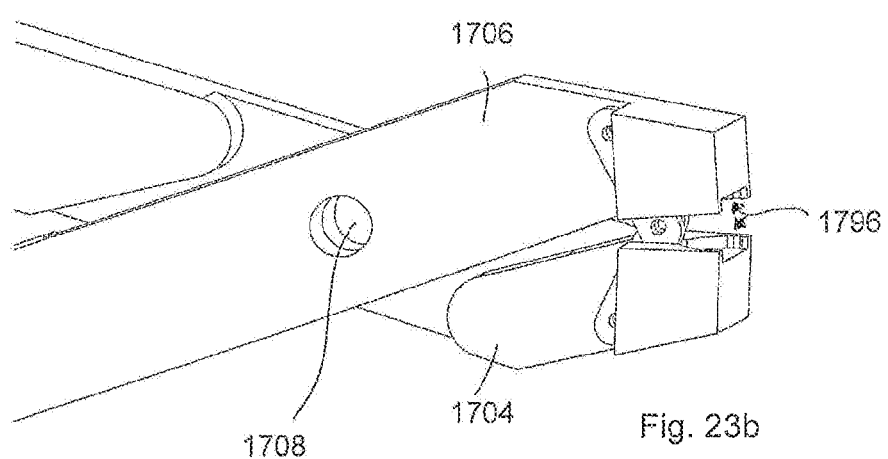
FIG. 23b shows an enlarged view of a tip portion of the pliers.

A sixth embodiment of an instrument in the form of pliers is shown with respect to FIGS. 21-22*c*. The pliers 1602 has arms or handles 1604, 1606, which are rotationally coupled to each other. The handles 1604, 1606 include tip portions which form a cavity 1696 similarly to the manner described above with respect to other tool or instrument embodiments. The arms 1604, 1606 have engagement structures 1681 projecting from respective ends of the cavity 1696 to engage engagement portions 51, 52 of a surgical staple 1, similar to the staple described according to the first embodiment.

Similar to the fifth embodiment of the instrument, a pressing portion 1682 is provided in the cavity by a separate part. Here, the pressing portion 1682 is a surface at a tip portion of a screw member 1610. As shown in FIG. 21, a threaded bore is provided in one or both of the handles 1604, 1606 to receive the screw member 1610 therein. FIGS. 22*a*-22*c* show a process of receiving and expanding the staple 1. First, in FIG. 22*a*, the handles 1604, 1606 can be brought closer together to expand the cavity 1696 to receive the bridge 2 of the staple 1, including extensions 5, 5' and/or engagement portions 51, 52. Here, the screw member 1610 can be retracted, while the staple 1 is inserted in the relaxed state, as shown in FIG. 22b. Next, the screw member 1610 is actuated or screwed-in to advance the pressing portion 1682 towards and against the top surface 21 of the bridge 2, indicated by the arrows in FIG. 22c. As a consequence, the staple 1 assumes its expanded state, where the bridge 2 is bent into a straight shape and the legs 3, 4 move away from each other to assume a parallel orientation. In a next step (not shown), the staple 1 may then be applied to one or more bones.

A seventh embodiment of an instrument, in another form of pliers, is shown with respect to FIGS. 23a-25d. The pliers 1702 has arms or handles 1704, 1706 which are rotationally coupled to each other. The handles 1704, 1706 include tip portions in which a cavity 1796 for holding a staple 1 is formed, similarly to the manner described above with respect to the other instrument embodiments.

However, unlike in the previous instrument embodiments, pliers 1702 provide for a combined movement of engagement structures 1781 and pressing portion 1782, which together form the cavity 1796 for expanding the surgical staple 1. The cavity 1796 extends parallel to an axis of rotation of the handles 1704, 1706 (e.g., see rotational shaft hole 1708 in FIG. 23a), rather than being perpendicular thereto as was the case in previous embodiments. Hence, when opening the handles 1704, 1706 or moving the handles 1704, 1706 away from one another, the cavity 1796 also opens and the staple 1 may be inserted into the cavity 1796 (see FIGS. 24a-24d). In this embodiment, the tip portions of handles 1704, 1706 include almost identical complementary shapes for forming the cavity 1796. When the handles 1704, 1706 are closed or moved towards one another, the cavity 1796 is also closed (see FIGS. 25a-25d), and the bridge 2 of the surgical staple 1 is safely received in the cavity 1796 in a form-fit manner.

Figure 24A:
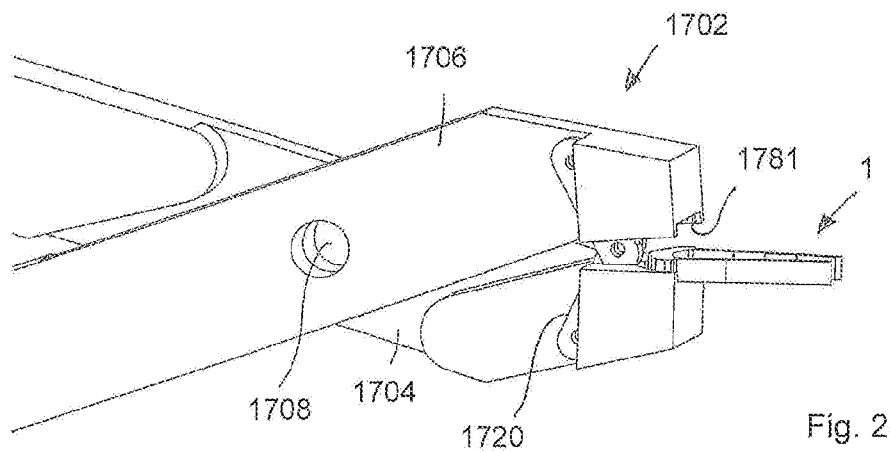
FIG. 24a shows an enlarged perspective view of a surgical staple and the tip portion of the pliers in a first step of a method for receiving, expanding, holding, and placing the staple in a bone, where the staple is received in a cavity at the tip portion of the pliers.
Figure 24B:
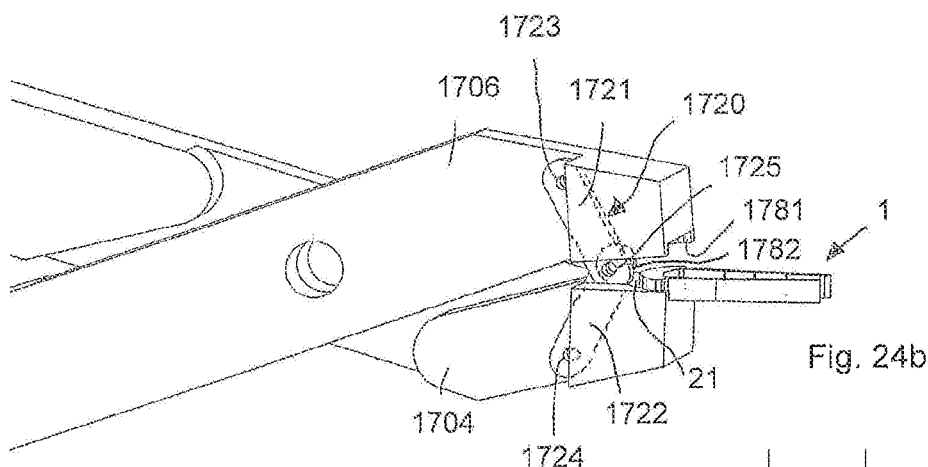
FIG. 24b shows a partial transparent view of the tip portion of the pliers of FIG. 24a to show details of a toggle lever of the pliers.
Figure 24C:
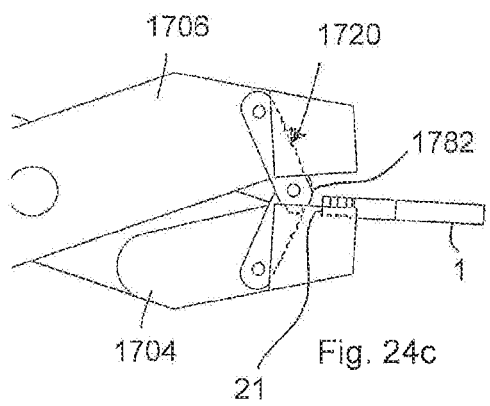
Figure 24D:
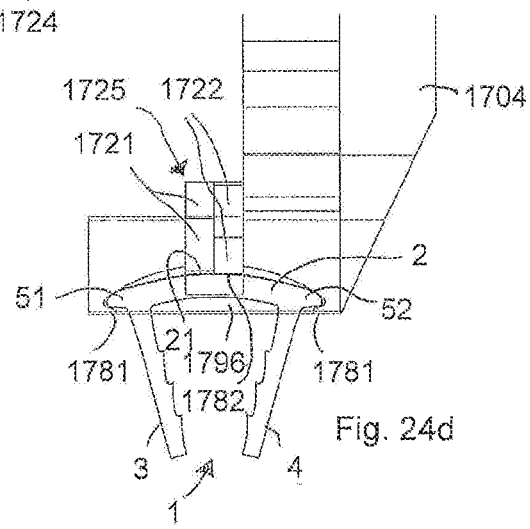
FIG. 24d shows a plan view of the tip portion of the pliers, including a bottom handle, a toggle joint, and the cavity at the tip portion of the pliers.

Expansion of the surgical staple 1 is effected by means of a toggle lever 1720, which is best seen in the partially transparent views of the instrument in FIGS. 24b and 25b. The toggle lever has two lever arms 1721, 1722, which are rotationally coupled at one end to tip portions of the handles 1704, 1706 via joints 1723, 1724, respectively. The other ends of both lever arms 1721, 1722 are rotationally coupled to each other via a joint 1725. Opening and closing the handles 1704, 1706 of the pliers 1702 thus also results in retraction and advancement of the mutually coupled ends of the lever arms 1721, 1722 to and from the cavity 1796. The mutually coupled ends of lever arms 1721, 1722 thereby form a pressing portion 1782 shaped and positioned to abut on a center portion of the bridge 2 when the pressing portion 1782 is advanced into the cavity 1796, in conjunction with a closing movement of the handles 1704, 1706, or when the handles 1704, 1706 are moved towards one another.

A twelfth embodiment of a surgical staple is explained with reference to FIGS. 27, 28a, and 28b. The surgical staple 2101 is similar to the staple 1 according to the first embodiment in that a bridge 2 has end sections 29, 29' at which there are provided respective extensions 5, 5', which form engagement portions 51, 52 for engagement by an instrument. However, this embodiment differs from the previously described embodiments of surgical staples with regard to the arrangement and geometry of barbs at respective legs 2103, 2104.

Figure 27:
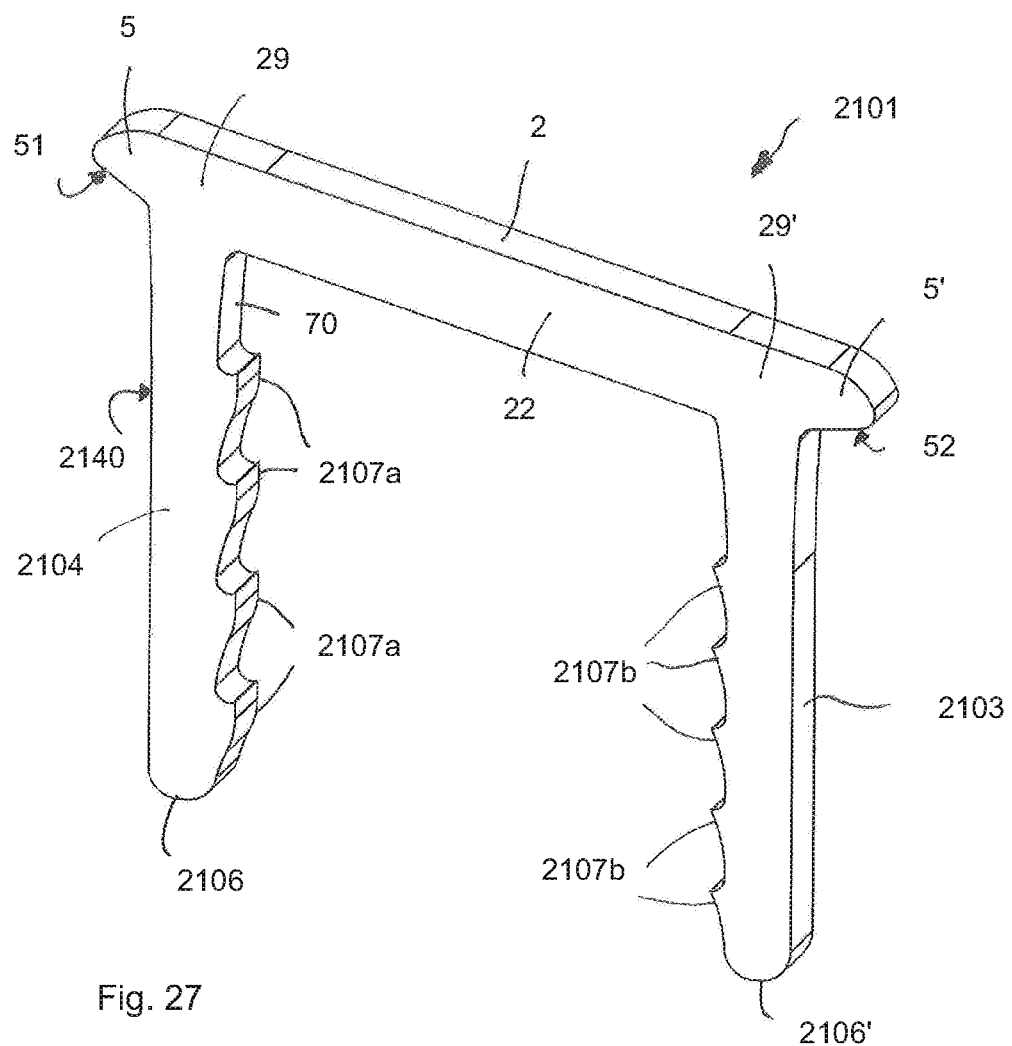
FIG. 27 shows a perspective view of a surgical staple according to a twelfth embodiment in an expanded state.

More specifically, as shown in FIG. 27, both legs 2103, 2104 are provided with barbs 2107a, 2107b which have a different geometry or tooth profile than the barbs 7 of the first to eleventh embodiments. In the previous embodiments, the overall size of the barbs 7 both along the lengths and perpendicular to the lengths of the legs 3, 4 is relatively small.

In this embodiment, barbs 2107a, 2107b are instead arranged and sized in view of the specific application of the surgical staple at an implantation site. For example, some bones or parts of bones, such as the central or diaphysis regions of bones, may generally involve regions with stiffer bone tissue, for example, where supply of bone tissue with blood is less prominent. In contrast, bone regions located closer to joints have more soft and spongy bone tissue.

Figure 28A:
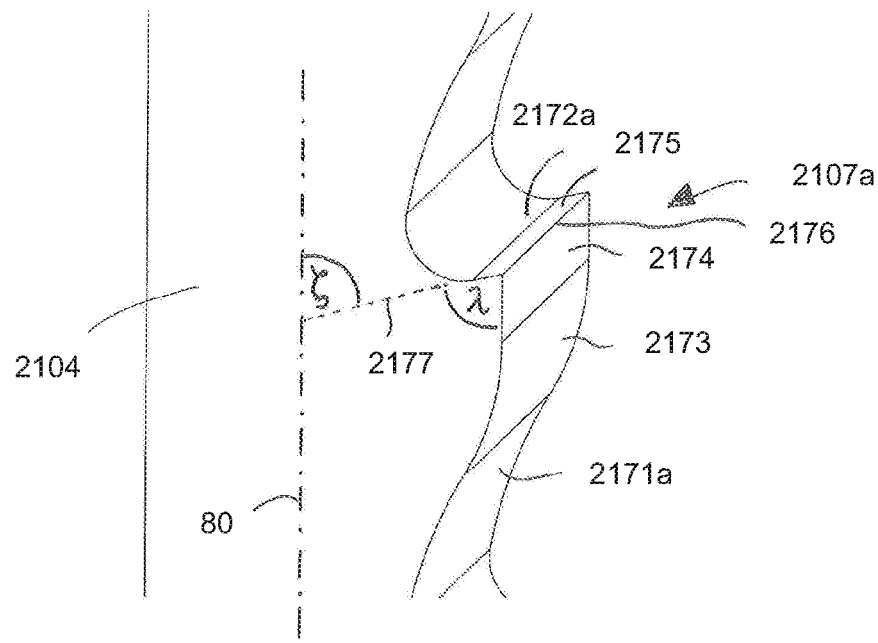
FIG. 28a shows an enlarged perspective view of a portion of a first leg of the staple of FIG. 27.

With regard to those regions having more soft bone tissue, for example, near a joint, a profile of teeth or barbs 2107a, as shown in FIGS. 27 and 28a, may be provided.

The barbs 2107a are more pronounced as compared with barbs 7 of the previous embodiments. The profile of adjacently arranged barbs 2107a resembles, for example, that of shark teeth. The height or extension of barb edges 2176 away from the leg 2104 may be larger as compared with the barbs in previous embodiments. Also, the length of the barbs 2017a measured along a length of the leg 2104 may also be larger, and adjacent barbs 2107a may continuously merge with each other at the legs 2104.

A shape of the barbs 2017a may include a concave shaped surface 2171a smoothly rising from a bottom of recesses between the barbs 2017a. That surface 2171a merges or continues into a convex shaped surface 2173, which in turn merges or continues into a substantially flat surface 2174, which may be substantially parallel to a line or plane 80 of the leg 2104. This profile smoothly compresses the adjacent soft bone tissue when the staple is driven into the bone and is released from the expanded state. Flat surface 2174 further forms the sharp edge 2176 together with a flat surface 2175, which steeply inclines on the side of the cutting surface of the barb 2017a. Flat surface 2175 defines a plane 2177 which forms an angle with line or plane 80 that is less than 90 degrees, for example, 70 to 85 degrees, and more preferably 75 to 80 degrees, in order to increase the barb function. The overhanging flat cutting surface 2175 bites or pierces into the adjacent soft bone tissue and improves the holding characteristics of the staple 2101. An angle λ formed at the barb edge between surfaces 2175 and 2176 is also less than 90 degrees, for example, 70 to 85 degrees, and more preferably 75 to 80 degrees. Concavely rounded surface 2712a then provides a steep transition towards the recess between adjacent barbs 2017a.

It may be noted that surface 2175 may also be slightly rounded, or may be part of steeply rising rounded surface 2172a with a similar concave curvature.

Figure 28B:
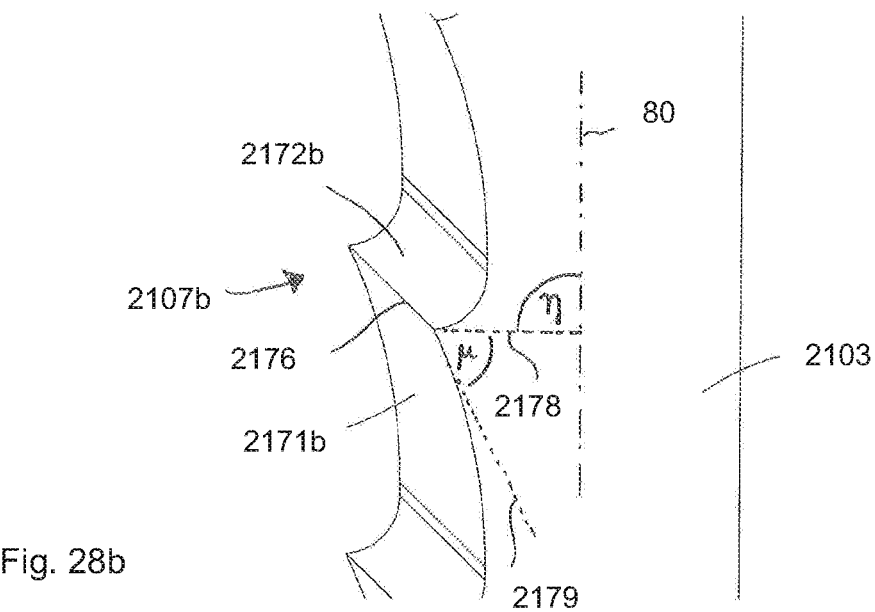
FIG. 28b shows an enlarged perspective view of a portion of a second leg of the staple of FIG. 27.

Another barb profile that may be more suited for stiffer tissue regions is displayed with respect to FIGS. 27 and 28b. Herein, a height or extension of barb edges 2176 of barbs 2107b away from the leg 2103 may be less than the height of barbs 2107a, such that a bite or piercing depth of the barbs 2107b into the stiffer bone tissue may be less. Moreover, the smoothly rising side of each barb 2107b may have only a concave shaped surface 2171b, without any convex shaped portions. Also, on the cutting side of each barb 2107b, there is a steeply rising rounded surface 2172b, which forms the barb edge 2176 together with surface 2171b. Adjacent the barb edge 2176, a plane or line 2179 tangential to steeply rising rounded surface 2712b forms an angle η n with a line or plane 80 of the leg 2103. In some embodiments, angle η may be formed to be 90 degrees or greater.

Moreover, surfaces 2171b and 2172b form a considerably more slender profile for the barb 2107b, compared with a profile of barb 2107a. An angle μ formed between tangential planes 2178 and 2179 of respective surfaces 2172b, 2171b may be about 50 to 80 degrees, and more preferably 60 to 70 degrees, which may be less than the angle A formed at the barb edge between surfaces 2175 and 2176 of barb 2107a. In other words, barb 2107b has a profile which is less pronounced, more slender, and oriented in a direction facing away from the leg 2103, as compared to the relationship between barbs 2107a and leg 2014.

FIG. 27 depicts a situation where a surgical staple 2101 has legs 2103, 2104 provided with different barbs 2107a, 2017b. Such a staple may be used, for example, for an osteotomy such as the one shown in FIG. 8d, with leg 2104 applied closer to a joint and leg 2103 applied farther away from the joint. However, alternatively or additionally, as also shown in FIG. 27, the number of barbs 2107a or 2107b on each leg 2103, 2104 may also be varied even within one staple 2101. Still further, the number of barbs per unit length may be varied even within one leg, for example, depending on the expansion forces visualized in FIG. 26. Still further, the profile of each of the barbs on each leg may also be varied or different from one another. For example, the barbs may be arranged asymmetrically or variably along the length of one leg, or in some embodiments both legs, such that the barbs are longer and/or have a larger profile or geometry near an end of the leg, while being shorter and/or having a smaller profile or geometry near a top of the leg closer to the bridge of the staple, for the staple to better grip the bone when implanted.

In contrast, it is also possible to provide one surgical staple with just one type of barb profile for both legs, without any variation. It is also possible, for example, to provide each leg with just one barb, or even no barbs, or to provide one leg with one or more barbs and the other leg with no barbs.

Many further modifications of the surgical staple and/or the instruments are also possible.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A surgical staple for compressing bone tissue, comprising:
    a first leg for anchoring in a first bone or bone fragment,
    a second leg for anchoring in a second bone or bone fragment, and
    an elastically deformable bridge monolithically formed with the first leg and the second leg, the bridge having a lower surface for seating against the bone tissue and an opposite upper surface, the bridge defining a longitudinal axis, the bridge having a first end section from which the first leg extends and a second end section opposite the first end section from which the second leg extends,
    a first engagement portion extending outward from the first end section, and having a lower surface elevated relative to the lower surface of the bridge, and
    a second engagement portion extending outward from the second end section and opposite and away from the first engagement portion, the second engagement portion having a lower surface elevated relative to the lower surface of the bridge,
    wherein in a relaxed configuration, the bridge is bent or curved such that a central region of the bridge is directed away from the first and second legs, and free ends of the first and second legs are positioned closer to one another than are portions of the first and second legs connected to the bridge.

2. The surgical staple of claim 1, wherein the longitudinal axis extends through the first and second engagement portions.

3. The surgical staple of claim 1, wherein the first and second engagement portions taper outward from the first and second end sections, respectively.

4. The surgical staple of claim 1, wherein the bridge is elastically deformable to orient the first and second legs parallel to each other, and
    when the first and second legs are parallel to each other, the lower surfaces of the first and second engagement portions are at an oblique angle relative to the lower surface of the bridge.

5. The surgical staple of claim 1, wherein the bridge is elastically deformable to orient the first and second legs parallel to each other, and
    when the first and second legs are parallel to each other, the lower surfaces of the first and second engagement portions are substantially parallel to the lower surface of the bridge.

6. The surgical staple of claim 1, wherein the surgical staple comprises a shape memory material exhibiting superelastic properties.

7. A surgical staple insertion system for compressing bones or bone fragments, comprising:
    a) the surgical staple of claim 1; and
    b) an insertion tool separately formed from the staple and having a first end and a second end, the second end defining a cavity configured to receive the first and second engagement portions and retain the bridge in a deformed configuration relative to the relaxed configuration with the first and second legs retained parallel to each other.

8. The system of claim 7, wherein the cavity is partially defined by first and second engagement structures that engage the lower surfaces of the first and second engagement portions, respectively.

9. The system of claim 8, wherein the first and second engagement structures have lower surfaces that do not extend lower than the lower surface of the bridge of the staple.

10. The system of claim 7, wherein the insertion tool consists of a unitary piece of material.

11. The system of claim 7, wherein the first and second engagement portions of the staple taper outward from the first and second end sections, respectively.

12. The system of claim 7, wherein the bridge is elastically deformable to orient the first and second legs parallel to each other, and
    when the first and second legs are parallel to each other, the lower surfaces of the first and second engagement portions are obliquely angled relative to the lower surface of the bridge.

13. The system of claim 7, wherein the bridge is elastically deformable to orient the first and second legs parallel to each other, and
    when the first and second legs are parallel to each other, the lower surfaces of the first and second engagement portions are substantially parallel to the lower surface of the bridge.

14. The system of claim 7, wherein the surgical staple comprises a shape memory material exhibiting superelastic properties.

15. A surgical staple for compressing bone tissue, comprising:
- an elastically deformable bridge having a lower surface for seating against the bone tissue and an opposite upper surface, a first end section, a second end section, a longitudinal axis extending between the first and second end sections, and a first side and a second side,
- a first leg at the first end section of the bridge for anchoring in a first bone or bone fragment,
- a second leg at the second end section of the bridge for anchoring in a second bone or bone fragment, the first and second legs monolithically formed with the bridge,
- a first engagement portion having a lower surface elevated relative to the lower surface of the bridge at located at one of the first end section and the first side, and
- a second engagement portion having a lower surface elevated relative to the lower surface of the bridge and located at one of the second end section and the second side,
- wherein in a relaxed configuration, the bridge is bent or curved such that a central region of the bridge is directed away from the first and second legs, and free ends of the first and second legs are positioned closer to one another than are portions of the first and second legs connected to the bridge.

16. The staple of claim 15, wherein the first and second engagement portions are located adjacent the first and second end sections of the bridge.

17. The staple of claim 15, wherein the first and second engagement portions are located along the first and second sides of the bridge.

18. The staple of claim 15, wherein the first and second engagement portions extend oppositely outward from the first and second end sections of the bridge.

19. The staple of claim 15, wherein the first and second engagement portions have lower surfaces that are obliquely angled relative to the lower surface of the bridge.

20. The staple of claim 15, wherein the first and second engagement portions have lower surfaces that are substantially parallel to the lower surface of the bridge.

21. A surgical staple insertion system for compressing bones or bone fragments, comprising:
a) the surgical staple of claim 15; and
b) an insertion tool separately formed from the staple and having a first end and a second end, the second end defining a cavity configured to receive the first and second engagement portions and retain the bridge in a deformed configuration relative to the relaxed configuration with the first and second legs retained parallel to each other.

22. The system of claim 21, wherein the cavity is partially defined by first and second engagement structures that engage the lower surfaces of the first and second engagement portions, respectively.

23. The system of claim 22, wherein the first and second engagement structures have lower surfaces that do not extend lower than the lower surface of the bridge of the staple.

24. The system of claim 21, wherein the insertion tool consists of a unitary piece of material.

25. The system of claim 21, wherein the bridge is elastically deformable to orient the first and second legs parallel to each other, and
when the first and second legs are parallel to each other, the lower surfaces of the first and second engagement portions are obliquely angled relative to the lower surface of the bridge.

26. The system of claim 21, wherein the bridge is elastically deformable to orient the first and second legs parallel to each other, and
when the first and second legs are parallel to each other, the lower surfaces of the first and second engagement portions are substantially parallel to the lower surface of the bridge.

27. The system of claim 21, wherein the surgical staple comprises a shape memory material exhibiting superelastic properties.

* * * * *